(12) United States Patent
Zhang et al.

(10) Patent No.: US 8,214,159 B2
(45) Date of Patent: Jul. 3, 2012

(54) APPARATUS AND METHOD FOR AUTOMATED QUALITY CONTROL

(75) Inventors: Jianzhong Zhang, Brea, CA (US); Arkadij M. Elizarov, Woodland Hills, CA (US); Reza Miraghaie, Culver City, CA (US); Carroll Edward Ball, Los Angeles, CA (US); Hartmuth C. Kolb, Playa Del Rey, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 336 days.

(21) Appl. No.: 12/630,298

(22) Filed: Dec. 3, 2009

(65) Prior Publication Data

US 2010/0145630 A1    Jun. 10, 2010

Related U.S. Application Data

(60) Provisional application No. 61/119,899, filed on Dec. 4, 2008.

(51) Int. Cl.
*G01N 31/00* (2006.01)

(52) U.S. Cl. ......................................................... 702/31

(58) Field of Classification Search ................... 702/31, 702/32, 33, 182–185, 188
See application file for complete search history.

(56) References Cited

U.S. PATENT DOCUMENTS

| | | | |
|---|---|---|---|
| 5,645,068 A | 7/1997 | Mezack et al. | |
| 5,835,384 A | 11/1998 | Lin | |
| 7,359,806 B2 | 4/2008 | Abraham-Fuchs et al. | |
| 7,519,492 B2 | 4/2009 | Miller et al. | |
| 7,610,157 B2 | 10/2009 | Miller et al. | |
| 2008/0064110 A1 | 3/2008 | Elizarov et al. | |
| 2008/0242915 A1 | 10/2008 | Jackson et al. | |
| 2010/0286512 A1* | 11/2010 | Dhawale et al. | ............. 600/431 |

FOREIGN PATENT DOCUMENTS

WO   WO 2008/141262 A1   11/2008

OTHER PUBLICATIONS

Moerlein, et al., Robotic Preparation of Sodium Acetate C 11 Injection for Use in Clinical PET, Published in Nuclear Medicine and Biology, vol. 29, No. 5, Jul. 1, 2002 (pp. 613-621).

Crouzel, et al., "Radiochemistry Automation for PET"; Radiopharmaceuticals for Positron Emission Tomography: Methodological Aspects Published in Kluwer Academic Publishers, 1993 (pp. 45-79).

International Search report in PCT/US2009/066694 dated Jul. 16, 2010.

(Continued)

*Primary Examiner* — Edward Raymond
(74) *Attorney, Agent, or Firm* — Joshua Ryan

(57) ABSTRACT

Methods and apparatus to assess current aspects of Quality Control useful for release of radioactive compounds for imaging, such as PET tracers as injectables, in an automated manner, without user interference, and in compliance with regulatory guidelines. The present method and system relates to an integrated automated quality control analysis of a substance utilizing a single sample injection for a plurality of inline quality control tests. A quantitative analysis of the sample via the plurality of quality control tests is conducted. A measurement value of each of the plurality of quality control parameters is determined and a comparison of each measurement value of the plurality of quality control parameters with a predetermined corresponding criterion value is made. A cumulative quality rating for the sample is determined and the validated sample is released based on the quality rating.

34 Claims, 19 Drawing Sheets

OTHER PUBLICATIONS

Peter J. H. Scott, Michael R. Kilbourn; Determination of Residual Kryptofix 2.2.2 Levels in [18F]-labeled Radiopharmaceuticals for Human Use; p. 1 of 1 (Abstract).

R. Nakao, T. Ito, M. Yamaguchi and K. Suzuki; Improved Quality Control of [F]FDG by HPLC with UV detection Nuclear Medicine and Biology; vol. 32, Issue 8, pp. 907-912 (Abstract).

Huanick; Direct Measurement of Kryptofix 2.2.2 in 18F-FDG by Gas Chromatography; received Oct. 24, 2006; revised Jan. 11, 2007; online Jun. 29, 2007; p. 1 of 1 (Abstract).

R. Nakao, T. Kida and K. Suzuki; Factors Affecting Quality Control of [$^{18}$F] FDG Injection: Bacterial Endotoxins Test, Aluminum Ions Test and HPLC analysis for FDG and CIDG; copyright © 2004 Elsevier Ltd.; Applied Radiation and Isotopes; vol. 62, issue 6, Jun. 2005 (Abstract).

Quality Control of PET Rediopharmaceuticals; Book: Molecular Imaging; Publisher: Springer Berlin Heidelberg;; Copyright: 2009; pp. 197-204; Subject Collection: Medicine; SpringerLink Date: Monday, Jul. 13, 2009 (Abstract).

Radiopharmaceutical Details: $^{18}$F-FDG by Brian Hockley; Divison of Nuclear Medicine; phone: (734) 615-2044; Fax: (734) 615-2557; email: hockley@umich.edu; pp. 1-4.

S. Yu, Review of $^{18}$F-FDG Synthesis and Quality Control; Department of Nuclear Medicine & PET and Experimental Surgery, Singapore General Hospital Singapore; received Aug. 1, 2006; received in revised form Dec. 20, 2006; accepted Dec. 30, 2006; Biomedical Imaging and Intervention Journal (Review Article).

Piyush Kumar, John Mercer, Courtney Doerkson, Katia Tonkin and Alexander J.B. McEwan; Clinical production, Stability Studies and PET Imaging with 16-α-[$^{18}$F]FES) in ER Positive Breast Cancer Patients; Received Mar. 1, 2007; Revision received Apr. 10, 2007; Accepted Apr. 14.

* cited by examiner

APPARATUS AND METHOD FOR AUTOMATED QUALITY CONTROL

CLAIM TO PRIORITY

The present application is based on and claims priority to U.S. provisional application No. 61/119,899, filed Dec. 4, 2008, which is hereby incorporated by reference in its entirety herein.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates generally to a system and method for automated quality control analysis of a compound. More specifically, the present invention relates to systems and methods for automated quality control analysis of a compound that utilizes a single sample injection for a plurality of inline quality control tests where some of the test stations are in line while others receive their sample via robotics and some do not require a sample.

BACKGROUND DISCUSSION

Quality Control (QC) devices and methods have become an increasingly important part of healthcare over the last few decades. Specifically in healthcare, QC has traditionally occurred at the site of the manufacturer, as opposed to the point of use. However, with the development of new contrast agents and other short half-life pharmaceutical products, it may be necessary to perform compounding or processing steps immediately prior to administration into a patient. Prior to injection, the safety and efficacy of the substance should be ensured. As such, Quality Control is important for radiosynthesized Positron Emission Tomography (PET) tracers that are to be used in clinical and research circumstances. The QC of radiotracers generally involves manual execution and subjective analysis in tests such as color and appearance, pH, radioactivity concentration, radiochemical purity, etc.

The quality requirements for radiotracers are set out in various pharmacopoeia including United States Pharmacopeia (USP), British Pharmacopeia (BP), European Pharmacopeia (EP), etc. It should be noted that the quality control requirements of various radiotracers differ among different countries as different countries may adopt a different set of standards.

SUMMARY OF THE INVENTION

One embodiment of the present invention is directed to an apparatus and method for automated quality control. The method is for an integrated automated quality control analysis of a compound that includes utilizing a single sample injection for a plurality of inline quality control tests. A quantitative analysis of the sample via the plurality of quality control tests is conducted and a measurement value of each of the plurality of quality control parameters is determined. Each measurement value of the quality control parameters is compared with a predetermined corresponding criterion value and a cumulative quality rating for the sample is determined. The validated sample is released based on the quality rating.

Another embodiment of the present invention is directed to the method described above and further includes a control parameter of particle and color content.

Yet another embodiment of the present invention is directed to the method described above and further includes a control parameter of filter membrane integrity.

Yet another embodiment of the present invention is directed to the method described above and further includes a control parameter of radionuclidic purity.

Yet another embodiment of the present invention is directed to the method described above and further includes a control parameter of radioactive concentration.

Yet another embodiment of the present invention is directed to the method described above and further includes a control parameter of pH of the sample solution.

Yet another embodiment of the present invention is directed to the method described above and further includes a control parameter of Kryptofix concentration.

Yet another embodiment of the present invention is directed to the method described above and further includes a control parameter of radiochemical identity.

Yet another embodiment of the present invention is directed to the method described above and further includes a control parameter of radiochemical purity.

Yet another embodiment of the present invention is directed to the method described above and further includes a control parameter of specific activity of the sample.

Yet another embodiment of the present invention is directed to the method described above and further includes a control parameter of bacterial endotoxin concentration.

Yet another embodiment of the present invention is directed to the method described above and further includes a control parameter of residual solvent concentration.

Yet another embodiment of the present invention is directed to the method described above and further includes determining a cumulative quality rating for the compound.

Yet another embodiment of the present invention is directed to the method described above and further includes releasing a validated dose of the sample based on the quality rating.

Yet another embodiment of the present invention is directed to the method described above and the compound includes a radiopharmaceutical, which may include a PET tracer.

Yet another embodiment of the present invention is directed to the method described above and further includes determining K222 concentration and solvent concentration from a single GC injection.

Yet another embodiment of the present invention is directed to the method described above and further includes determining K222 concentration by GC.

Yet another embodiment of the present invention is directed to the method described above and further includes determining specific activity from a single HPLC injection.

Yet another embodiment of the present invention is directed to the method described above and further includes performing a microfluidic K222 test.

Yet another embodiment of the present invention is directed to an apparatus, or a system, for an automated quality control analysis of a PET tracer sample. The apparatus includes an injection valve to deliver the sample from a vial via a syringe in to the sample line. There is at least one sample line filled with the sample for a plurality of quality control tests. The apparatus also includes a distribution valve and station for testing the integrity of a filter membrane. Furthermore, an optical cell that is used for color and/or appearance testing is connected to a light source and/or a laser and a spectrometer via fiber optics. The apparatus also includes an HPLC pump, a HPLC column, a UV cell connected to a UV light source and a UV detector via fiber optics. The apparatus also includes radioactivity detection modules, a GC column, and a pH test cell with a pH electrode. The tests are performed using the various modules and a processor is used for quantitative processing of the experimental data and generation of a report reflecting the quality of the sample against predetermined standards.

Yet another embodiment of the present invention is directed to the apparatus described above and the apparatus is portable.

Yet another embodiment of the present invention is directed to the apparatus described above and further including radiation shielding disposed proximal to one or more of the elements.

Yet another embodiment of the present invention is directed to the apparatus described above in which the computer system is located remotely from the apparatus.

Yet another embodiment of the invention is directed to a quality control system that includes an apparatus for automated quality control analysis of a sample; and a synthesis module for originating the sample. The apparatus comprises the following elements:

- an introduction module configured to deliver the sample from a vial;
- at least one sample line filled with the sample for a plurality of quality control tests;
- a distribution valve;
- a filter membrane integrity test setup;
- an optical cell for color and for appearance test connected to a light source and/or a laser and a spectrometer via fiber optics;
- a HPLC column;
- a UV cell connected to a UV light source and a UV detector via fiber optics;
- a radioactivity detection module;
- a GC column;
- a pH test cell;
- one or more ports to operatively couple the elements to a computer system for quantitative processing of the experimental data and generation of a report reflecting the quality of the sample against the predetermined standards.

Yet another embodiment of the present invention is direct to the system as described above wherein the vial includes radiation shielding.

Yet another embodiment of the present invention is direct to the system as described above wherein the apparatus is operatively coupled to the synthesis module.

Yet another embodiment of the present invention is direct to the system as described above wherein the apparatus is fluidically coupled to the synthesis module.

Yet another embodiment of the present invention is direct to the system as described above wherein the apparatus is mechanically coupled to the synthesis module.

Yet another embodiment of the present invention is direct to the system as described above wherein the apparatus is electronically coupled to the synthesis module.

Additionally other embodiments of the present invention include:

1. Inline structure: one injection fills the majority of the test modules.
2. Variable radioactivity detection sensitivity: greatly reduces the analysis time.
3. GC test for both organic solvents and Kryptofix.
4. One optical cell for both color and appearance (clarity) tests.
5. Pressure drop for filter membrane test.
6. Microfluidics Kryptofix test.

These and other various embodiments of the present invention, together with the organization and manner of operation thereof, will become apparent from the following detailed description when taken in conjunction with the accompanying drawings. The entire disclosures of all patents and references cited throughout this application are incorporated herein by reference in their entirety.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

Embodiments of the invention are described by referring to the attached drawings, in which.

DETAILED DESCRIPTION

Figure 1A:
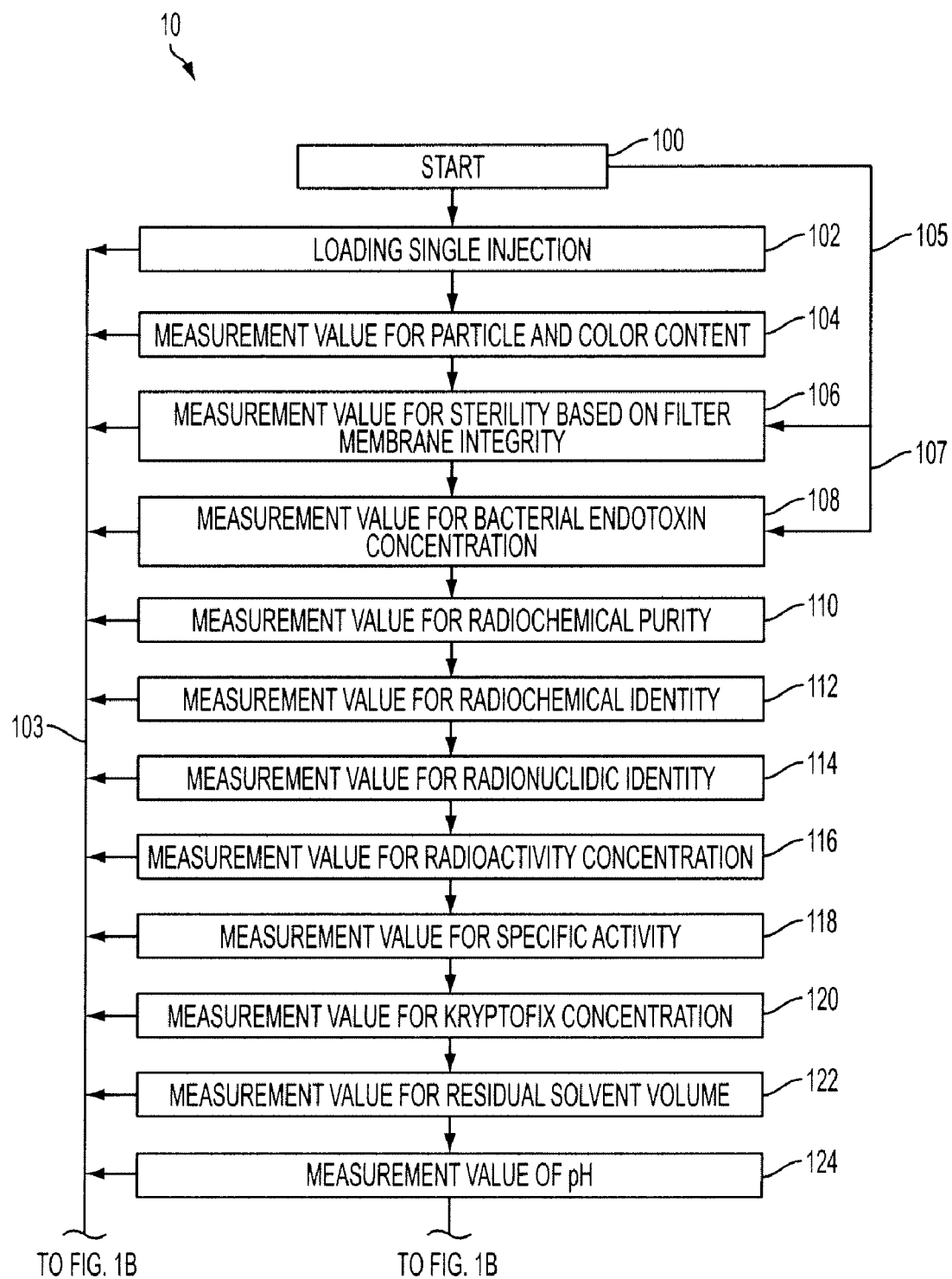
FIG. 1 illustrates a flowchart of steps according to an embodiment of the present invention.

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions.

As used in this application, the terms "component" and "system" are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

There are disclosed, as various embodiments of the present invention, methods and apparatus for performing an automated quality control test for a plurality of control parameters. For example, embodiments of the present invention include a plurality of tests.

Typical manual QC (quality control) operation for PET tracers is labor intensive and time consuming. Some results of manual tests rely on the interpretation of experienced operators. The manual operation presents hazardous exposure to the operators. Also many aspects of manual QC rely on non-quantitative data and the pharmacist's opinion.

An automated QC system according to embodiments of the present invention may be used, for example, for radio-synthesized tracers, covering a plurality of tests, which assess, for example: 1. particle and color content; 2. sterility based on filter membrane integrity; 3. radionuclidic purity; 4. radioactive concentration; 5. pH of a sample solution; 6. Kryptofix concentration; 7. radiochemical identity; 8. radiochemical purity; 9. specific activity of the sample; 10. bacterial endotoxins concentration; and 11. residual solvent volume.

The embodiments of the present invention enable simplified and automated operation. The test results are quantitative, the testing modules are inline, and the tests may be performed in parallel. As a result, the test results are more reliable, the operator is less susceptible to radiation, and the whole process is more economical and efficient as time and labor for the QC are significantly reduced.

Furthermore, as stated herein, embodiments of the present invention provide a single injection sample test procedure for multiple parameters to determine acceptability of the sample. Each specific test has associated predetermined criteria that the sample must pass. The time for performing all the inline tests is approximately 15 minutes; but a single operator, or technician may supervise the testing since parameter takes less than a minute to perform, using the automated inline methods and apparatus described herein.

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions. Some Definitions:

A "radiolabeled compound" is a compound where one or more of the atoms of the molecule is substituted for a radioactive isotope, such as in radioactive tracing. Radiolabeled compounds are compounds that can bind target sites in the body, including, but not limited to, for example, the brain.

The term "radioactive isotope" refers to isotopes exhibiting radioactive decay (e.g., emitting positrons). Such isotopes are also referred to in the art as radioisotopes or radionuclides. Radioactive isotopes or the corresponding ions, such as the fluoride ion, are named herein using various commonly used combinations of the name or symbol of the element and its mass number and are used interchangeably (e.g., 18F, [18F], F-18, [F-18], fluorine-18). Exemplary radioactive isotopes include 124I, 18F, 11C, 13N and 15O, which have half-lives of 4.2 days, 110 minutes, 20 minutes, 10 minutes, and 2 minutes, respectively.

Positron Emission Tomography (PET) is a molecular imaging technology that is increasingly used for detection of disease. PET imaging systems create images based on the distribution of positron-emitting isotopes in the tissue of a patient. The isotopes are typically administered to a patient by injection of probe molecules, which comprise a positron-emitting isotope, e.g. carbon-11, nitrogen-13, oxygen-15, or fluorine-18, attached to a molecule that is readily metabolized or localized in the body or that chemically binds to receptor sites within the body. The short half-lives of the positron emitters require that synthesis, purification and analysis, such as QC of the probes are completed rapidly. Such compounds include, but are not limited to 18F-FLT ([18F]fluorothymidine), 18F-FDDNP (2-(1-{6-[(2-[F-18]fluoroethyl)(methyl)amino]2-naphthyl}ethylidene)malonitrile), 18F-FHBG (9-[4-[18F]fluoro-3-(hydroxymethyl)butyl]guanine or [18F]-penciclovir), 18F-FESP ([18F]-fluoroethylspiperone), 18F-p-MPPF (4-(2-methoxyphenyl)-1-[2-(N-2-pyridinyl)-p-[18p]fluorobenzamido]ethylpiperazine) and 18F-FDG ([18F]-2-deoxy-2-fluoro-D-glucose).

"Radioactivity concentration" is an amount of any specified radioisotope in a sample and is usually measured as Curies per Liter, where Curie Per Liter (Ci/L) has a dimension of $L^{-3}T^{-1}$ where L is length, and T is time.

"Kryptofix" or "K222" is a tradename for commercially available cryptands. Cryptands are a family of synthetic bi- and polycyclic multidentate ligands for a variety of cations. These molecules are three dimensional analogues of crown ethers but are more selective and complex. The most common and most important cryptand is $N[CH_2CH_2OCH_2CH_2OCH_2CH_2]_3N$. This compound is termed [2.2.2]cryptand where the numbers indicate the number of ether oxygen atoms (and hence binding sites) in each of the three bridges between the amine nitrogen "caps". All-amine cryptands exhibit particularly high affinity for alkali metal cations, which has allowed the isolation of salts of $K^-$.

Bacterial endotoxins include, for example a concentration that is a component of gram-negative bacterial cell walls. Endotoxins are, for example, toxins associated with certain bacteria. It is possible to perform a test for this parameter using an integrated device, such as Endosafe-PTS™, made by Charles River to test endotoxin content. The device uses a cartridge to handle the QC and reference samples. There is a range of measurement value in the unit of EU/ml.

The term "column" means a device that may be used to separate, purify or concentrate chemical compounds. Such columns include, but are not limited to, various types of High-Performance Liquid Chromatography (HPLC) columns and Gas Chromatography (GC) columns. For example, HPLC is liquid phase separation/detection instrument. GC is gas phase separation/detection instrument. Both HPLC and GC use columns. HPLC usually uses a packed column whereas the GC typically uses a coated capillary column.

The term "sample" generally refers to a homogeneous or a heterogeneous fluid. Solution is an example of a homogeneous fluid. Heterogeneous fluid such as, for example, a suspension or slurry, contains solid particles, for example, insoluble reagents or products, or beads (reagents on solid support). Heterogeneous fluids also include emulsions or colloids. Embodiments of the present invention typically have better results with homogenous solutions since such solutions are typically provide better results, especially with respect to color and appearance tests.

Some examples of the radiolabeled compounds that may be analyzed according to one or more embodiments of the present invention include compounds selected from the group of 2-deoxy-2-[18F]fluoro-D-glucose ([18F]FDG), 6-[18F]fluoro-L-3,4-dihydroxyphenylalanine ([18F]FDOPA), 6-[18F]fluoro-L-meta-tyrosine ([18F]FMT), 9-[4-[18F]fluoro-3-(hydroxymethyl)butyl]guanine ([18F]FHBG), 9-[(3-[18F]fluoro-1-hydroxy-2-propoxy)methyl]guanine ([18F]FHPG), 3-(2'-[18F]fluoroethyl)spiperone ([18F]FESP), 3'-deoxy-3-[18F]fluorothymidine ([18F]FLT), 4-[18F]fluoro-N-[2-[1-(2-methoxyphenyl)-1-piperazinyl]ethyl]-N-2-pyridinyl-benzamide ([18F]p-MPPF), 2-(1-{6-[(2-[18F]fluoroethyl)(methyl)amino]-2-naphthyl}ethylidine)malononitrile ([18F]FDDNP), 2-[18F]fluoro-α-methyltyrosine, [18F]fluoromisonidazole ([18F]FMISO) and 5-[18F]fluoro-2'-deoxyuridine ([18F]FdUrd).

Figure 1B:
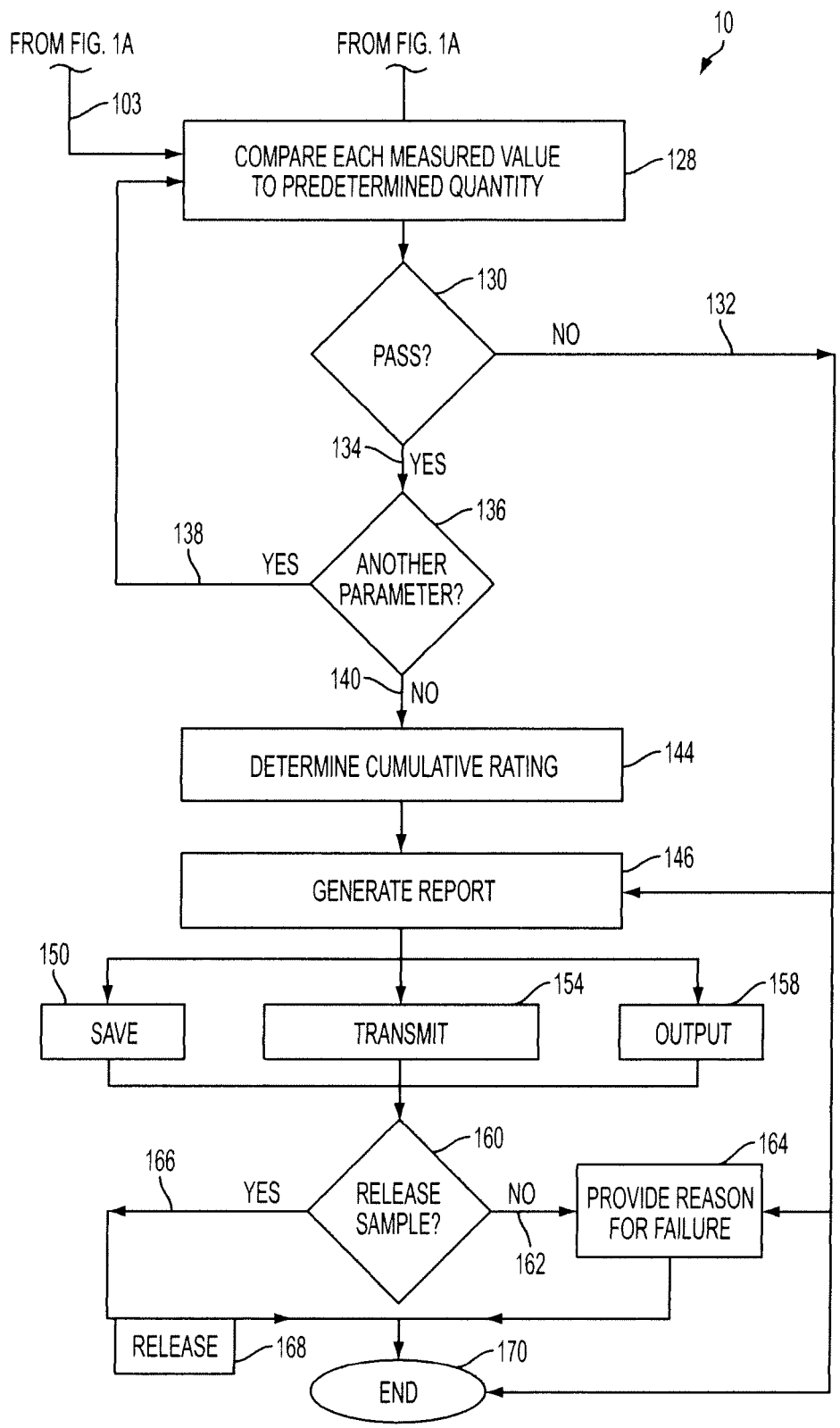

FIG. 1 illustrates a flowchart of steps 10 according to an embodiment of the present invention. Flowchart 10 is typically, for example, a series of steps or program code, such as executable, or computer code, that maybe stored on a computer-readable medium or other electronic storage medium, such as a RAM, ROM, EEPROM, CD, DVD, non-volatile memory, removable memory card or non-transitory electronic storage medium. The steps 10 may be executed by a processor, or otherwise executed or implemented to perform the identified functions and may also be stored in one or more electronic memories.

The method shown in FIG. 1 is used for an automated quality control analysis of an agent, such as a PET tracer, and includes a start step 100. The process shown in FIG. 1 is in-line because the same sample, from a single injection, or source is used to perform quality testing. Step 102 shows that a single injection of a sample is loaded for complete analysis. In step 104, a measurement value for particle and color content is determined. In step 106, a measurement value for sterility based on a filter membrane integrity (after the entire amount of product has been passed through it) is determined. The filter membrane test is primarily used to ensure its integrity after use. In step 108, a measurement value for bacterial endotoxins concentration is determined. As shown by line 105, the test for filter membrane integrity does not require any sample. Also, as shown by line 107, the endotoxin concentration test may use additional sample loading. The filter membrane integrity test and the endotoxin concentration test are two separate tests.

In step 110, a measurement value for radiochemical purity is determined.

In step 112, a measurement value radiochemical identity is determined. In step 114, a measurement value for radionuclidic purity is determined. In step 116, a measurement value of radioactivity concentration is determined. In step 118, a measurement value for specific activity is determined. In step 120, a measurement value for Kryptofix concentration is determined. In step 122, a measurement value for residual solvent volume is determined. In step 124, a measurement value for pH of the sample solution is determined. In step 128, a comparison is made between each measured value and an associated predetermined quantity to determine whether each measured parameter is satisfactory, i.e., "passes". Step 128 is also reached via line 103 which shows that the measurement of parameters can be parallel.

Indeed, each test may be performed while the other tests are being performed. That is, all the measurements do not be performed in a sequence. This feature of parallel determinations enhances the speed at which the tests can be performed. Step 130 shows that each measured parameter must pass the associated test for the sample to pass. Specifically, "no" line 132 shows that a step of generating a report (146) and/or providing the reason for the failure (164) as well as end step 170 is reached if the sample does not pass each test.

When a sample passes a particular test, "yes" line 134 leads to step 136 which determines whether all desired test parameters have been accounted. If there are additional parameters, "yes" line 138 leads to step 128. When all desired parameters are identified and have deemed satisfactory, a cumulative rating for the sample is determined in step 144 via line 140. A report is generated in step 146. This report can provide an explanation of each test performed and the result of each test. The report may be saved, step 150, transmitted, step 154, and/or output, step 158.

A determination whether to release the sample is made in step 160. If so, "yes" line 166 shows that the sample is released as shown in step 168 and end step 170 is reached.

Figure 2A:
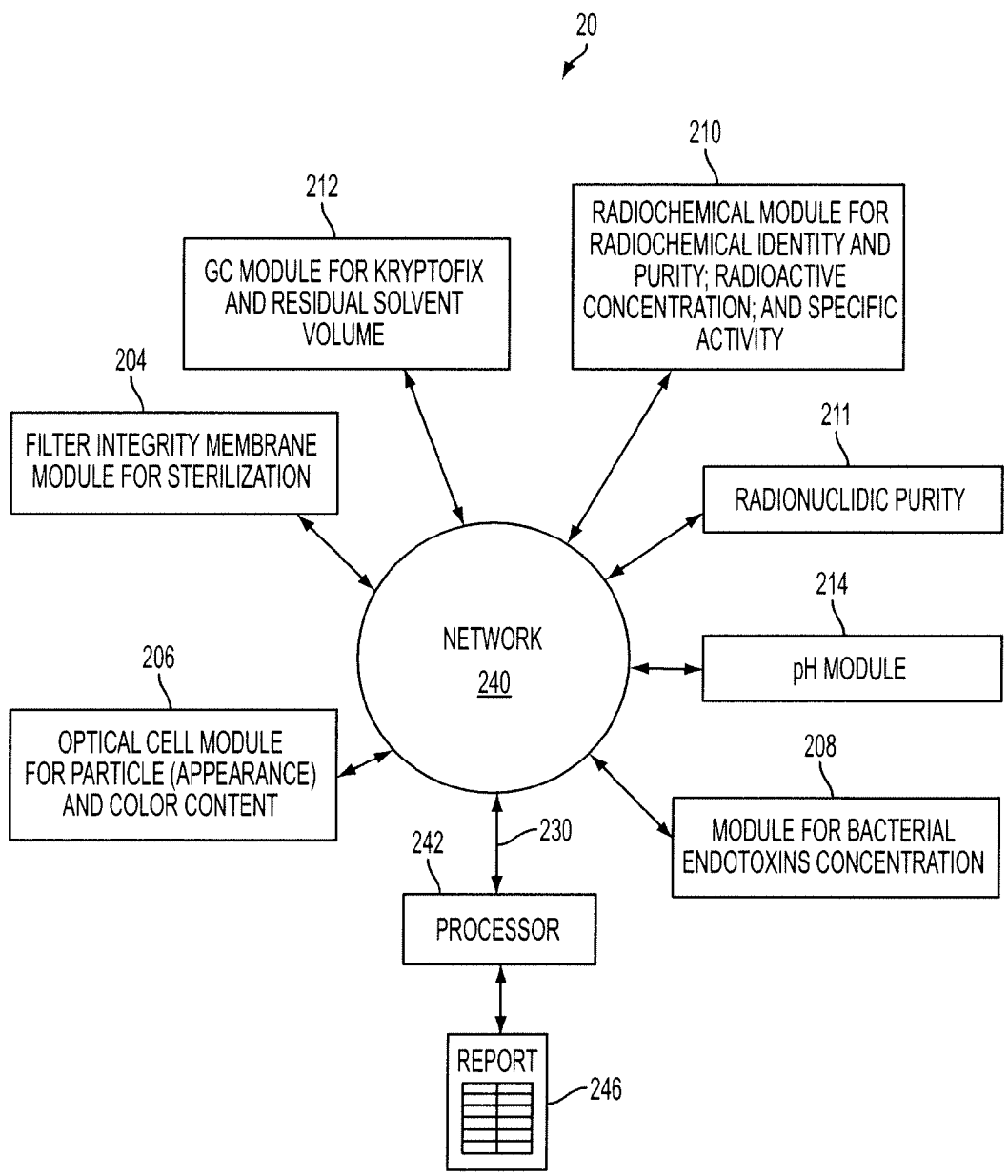
FIGS. 2A and 2B illustrate embodiments of apparatuses in accordance with the present invention.

Even though a sample passes each test, the sample may not be released for another reason, as shown by "no" line 162 that shows a report providing the reason for failure may be generated as shown in step 164. The reason for such a failure, other than failing a particular test, may be improper test conditions, inadequate sample size or other basis. End step 170 is then reached FIG. 2A shows a schematic of an apparatus, or QC system, 20 of a plurality of testing modules used for quality control. As shown in FIG. 2A, system 20 is a network system in which various testing modules are operatively coupled to one another and processor module 242 via network 240.

The network 240 is, for example, any combination of linked computers, or processing devices, adapted to transfer (transmit and/or receive) and process data. The network 240 may include wireless and wired transmission capabilities. The network 240 may be a private Internet Protocol (IP) network, as well as a public IP network, such as the Internet that can utilize World Wide Web (www) browsing functionality. Alternatively the network 240 may be an Ethernet network, or any two or more operatively coupled processing devices that can share information.

An example of a wired network is a network that uses communication busses and MODEMS, or DSL lines, or a local area network (LAN) or a wide area network (WAN) to transmit and receive data between terminals (such as processor 242 and testing or measurement modules 204, 206, 208, 210, 211, 212 and 214). An example of a wireless network is a wireless LAN. Global System for Mobile Communication (GSM) is another example of a wireless network. The GSM network is divided into three major systems which are the switching system, the base station system, and the operation and support system (GSM). Also, IEEE 802.11 (Wi-Fi) is a commonly used wireless network in computer systems, which enables connection to the Internet or other machines that have Wi-Fi functionality. Wi-Fi networks broadcast radio waves that can be picked up by Wi-Fi receivers that are attached to different computers. As shown in FIG. 2A, the network 240 is coupled to processing device 242 via wired or wireless bi-directional communication medium 230.

The apparatus 20 may be used for inline testing for performing a plurality of tests for quality control. For example, particle and color content module 206 is used for determining particle and color parameters. For example, this test compares an identified color with a predetermined range for color acceptability.

Figure 3:
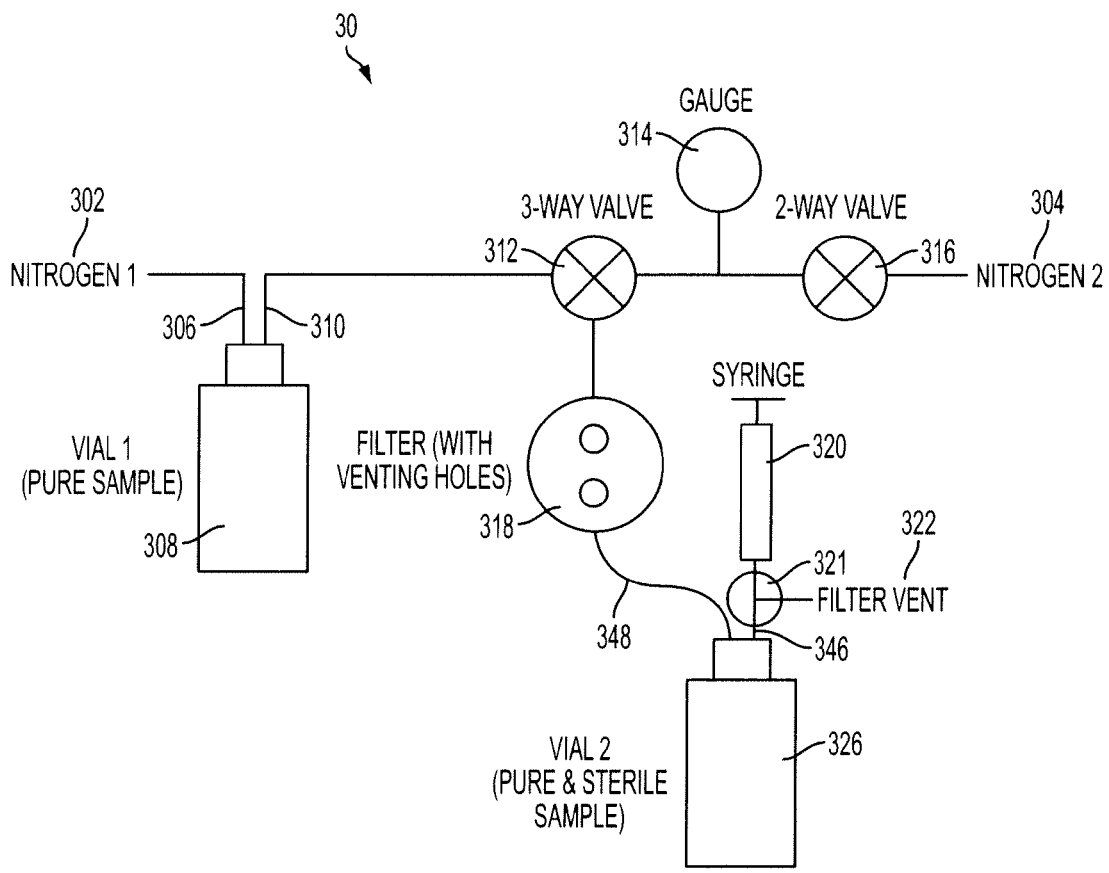
FIG. 3 shows a schematic for a filter membrane integrity test.

Filter membrane integrity module 204 is used to determine sterility of a sample based on the speed of a pressure drop after the membrane has been pressurized with gas (after it has been used for filtering the product. A schematic for the filter membrane integrity test is shown in FIG. 3.

Figure 5:
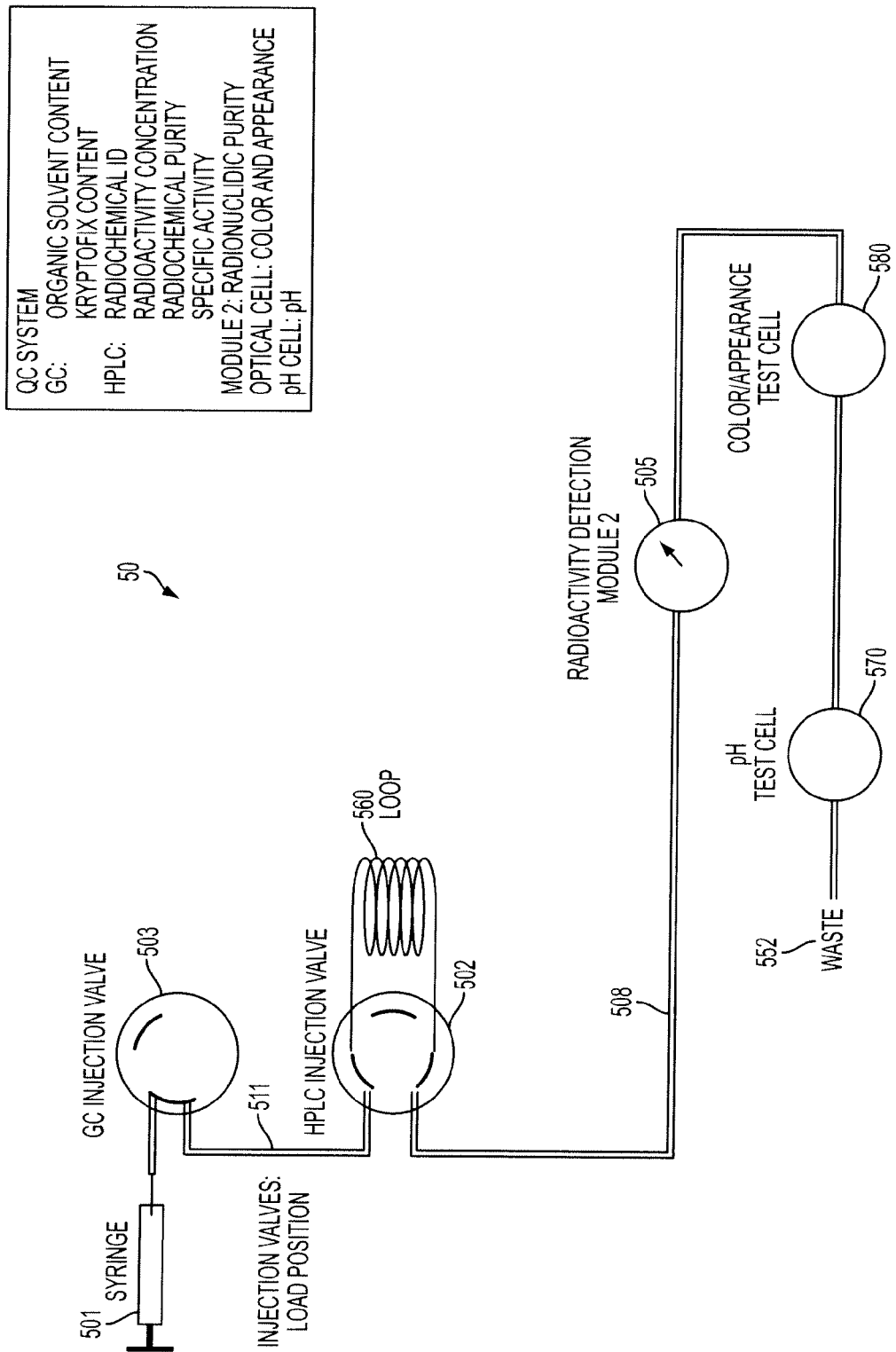
FIG. 5 shows a schematic including GC unit, HPLC unit, radionuclidic purity unit, color and appearance (clarity) unit and pH unit.
Figure 12:
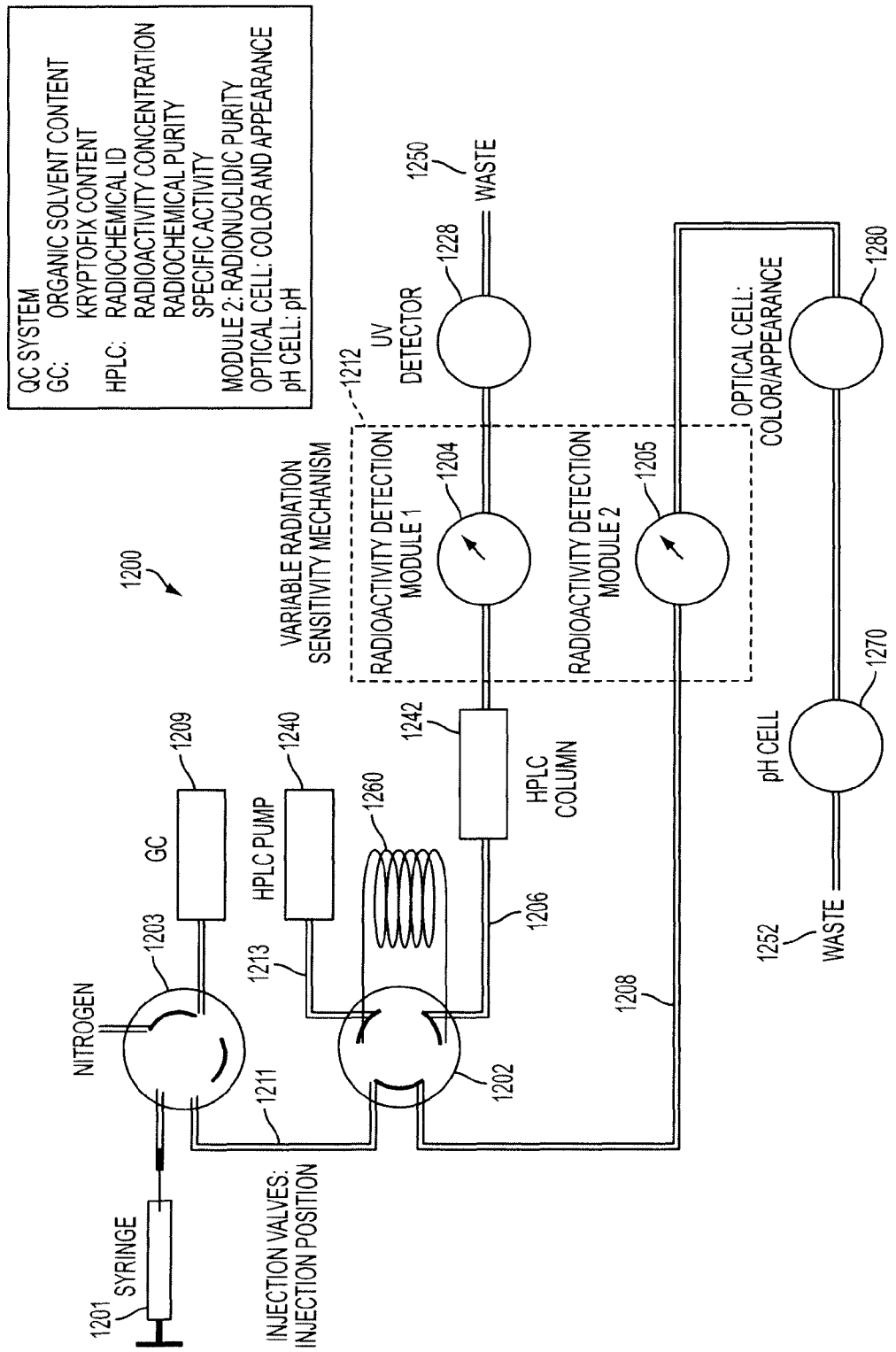
FIG. 12 shows a schematic for test parameters according to an embodiment of the present invention.

Radiochemical module 210 is used for determination of radiochemical identity, radiochemical purity, radioactive concentration and specific activity. A schematic for these tests is shown in FIGS. 5, and 12.

Radionuclidic purity module 211 is used to determine the radionuclidic purity of a sample. A schematic for this test is shown in FIGS. 5 and 12.

A pH of a sample solution is determined using pH module 214. A schematic for the pH test is shown in FIG. 5.

A GC module 212 is used for determination of Kryptofix concentration and residual solvent concentration. A schematic for the Kryptofix test is shown in FIG. 5.

A bacterial endotoxins concentration module 208 performs endotoxins test, which are toxins associated with certain bacteria.

Processor module 242 is used to compare control parameters, obtained from the modules described above with predetermined corresponding criterion values and to generate a cumulative quality rating for the sample.

Report module 246 is used to generate a report for the sample based on the quality rating. This report can be transmitted to a pharmacist or a researcher to provide information for a dose sample of a biomarker to be further used in clinic or research. The report can be transmitted via network 240 to another destination (not shown).

Each module described above may be coupled to one or more processing modules. While a single processing module 242 is shown for description purposes, additional processing modules may be used for efficiency.

Figure 2B:
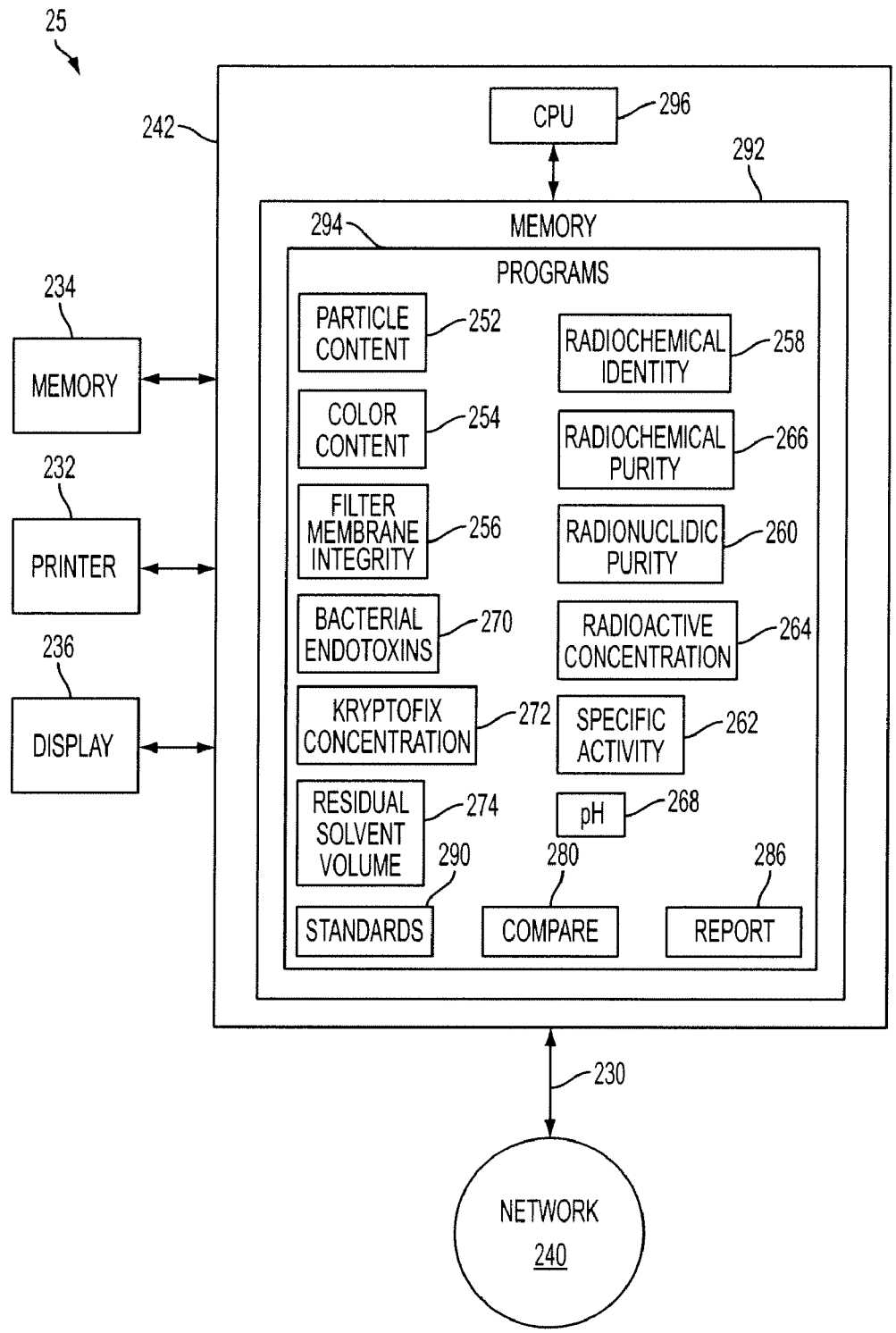

FIG. 2B shows another embodiment 25 of an apparatus according to the present invention. FIG. 2B shows modules as part of a processing device 242. The modules of FIG. 2B are typically program code that include algorithms to calculate values based on measured data, as shown in FIG. 2A.

Processor unit, or module 242 is typically a system control unit that generates a report, performs processing and transmits the data over network 240, displays (236), and/or prints (232) and/or stores (234) the processed data.

Processor unit 242 typically includes a CPU 296 and memory 292 to perform the necessary data processing and storage functions.

Processing unit, or device, or module, or terminal, 242 is typically one or more computers, or other processing device(s), wireless processing device, personal computer (PC), desktop, notebook, information appliance and the like. The processing device 242 typically includes processing (296) and storage (292) modules. The processor 242 is coupled to network 240 via bi-directional communication medium 230.

The image display unit, or module, 236 is coupled to processor unit 242 via bidirectional communication medium, which is typically a bus or wired connection or wireless connection. The display unit 236 is used to display the report or output data generated processor module 242. The display unit 236 may be, for example, a monitor, LCD (liquid crystal display), a plasma screen, a graphical user interface (GUI) or other module adapted to display output data typically by a representation of pixels.

The processing module 242 may also be coupled to a printer 232 to print the output, or a transmission module, such as a DSL line (not shown) or a modem, such as a wireless modem (not shown), to transmit the output to a second location or another display module. This transmission may also be accomplished using a network 240, such as the Internet, with web browsing capability, or other network of operatively coupled computers, processors, or output devices. Memory module 234 is additional electronic storage device and can be used to store data.

Memory module 292 is, for example, an electronic storage medium, such as a server, or other electronic storage repository that can store data. The memory module 292 may include, for example, RAM, ROM, EEPROM or other memory media, such as an optical disk, optical tape, CD, or a floppy disk, a hard disk, or a removable cartridge, on which digital information is stored in the form of bits. The memory module 292 is shown as coupled to processing module 296 via wired or wireless bi-directional communication medium. The memory module has program storage 294.

The CPU 296 is typically a processor that includes an arithmetic logic unit (ALU), which performs arithmetic and logical operations, and a control unit (CU), which extracts instructions from memory and decodes and executes them, utilizing the ALU when necessary.

Memory module 292 is typically an electronic storage medium such as RAM, ROM, EEPROM or other memory device, such as an optical disk, optical tape, CD, or a floppy disk, a hard disk, or a removable cartridge, on which digital information is stored in the form of bits. It may also include recorders to record to and read from mass storage devices such as, for example, optical disks, magnetic disks, flash semiconductor disks, and other types of storage which may be temporary or permanent.

The memory module 292 stores programs in program module 294. Program module 294 includes, for example, a web browser (not shown), particle content module 252, color content module 254, filter membrane integrity module 256, bacterial endotoxin module 270, Kryptofix concentration module 272, residual solvent volume module 274, radiochemical identity module 258, radiochemical purity module 266, radionuclidic purity module 260, radioactive concentration module 264, specific activity module 262, pH module 268. Standard storage module 290, comparison module 280 and report module 286. Each of these modules perform the associated function described herein.

Standard storage module 290 is used to store predetermined criteria for various parameters. Comparison module 280 makes a comparison between each measured value and an associated predetermined quantity to determine whether each measured parameter is satisfactory, i.e., "passes". Report module 286 generates a report identifying the outcome of each test and whether the sample passed all of the tests.

The processing module 242 also includes typical operating system programs (not shown), input/output programs (not shown), and other programs that facilitate operation of processing device 242.

Memory module, or facility, 292 is used to store used or generated by the CPU 296. The memory 292 may be accessed in such a way that the contents of the memory are provided to the CPU 296. Once the data has been accessed, typically by program code to fetch, or retrieve, the desired data stored in memory, it may be processed according to one or more algorithms described here.

FIG. 3 illustrates an example of a setup 30 for performing a filter integrity test.

Typically, liquid pharmaceutical and biopharmaceutical products are sterilized by filtration. The sterilizing filtration process is designed to remove viable and non-viable particles from the liquid passing through the filter. The particles removed from the fluid either remain on the surface of the filter membrane or are trapped within the membrane matrix. Integrity testing relies on the measurement of gas flow through wetted membranes. Diffusion of the test gas through the liquid filled pores in the membrane is a function of the diffusion constant and the solubility of the test gas in the liquid at the test temperature, the pressure differential of the test gas across the membrane, the thickness of the liquid layer, and the area and porosity of the membrane. Usually, after wetting the filter material, a gas pressure is applied to the inlet side and preferably the diffusive flow through the wetted filter material measured. The pressure is then measured in the outlet conduit as a function of time. It is then determined whether the pressure measured at a preselected time exceeds a reference pressure by a pre-determined amount. The filter is used to sterilize a sample, for example a PET tracer. This test is to make sure the filter membrane is still in good condition or maintains its integrity after the filtration has been completed. Otherwise the PET tracer is questionable. While the test may damage the membrane, that is not critical or important at the test stage. The significance of the test is whether at a threshold pressure the filter is still acceptable or not.

It should be noted that the filter 318, features small venting holes. A filter device (shown in FIG. 11) is designed to block the venting holes at the time of the filter membrane integrity test. Otherwise, the venting holes remain open. Upon opening a valve, for example a 3-way valve, 312 to nitrogen source 302, the pressure from the nitrogen source 302 pushes the purified sample solution out of the vial 308 and fills the vial 326 through the filter 318, a process used to sterilize the tracer sample. An aliquot of the sample can be taken out from the vial 326 for the following QC tests with the syringe 320. The sterile sample vial may also be equipped with an additional filter vent 322. The filter vent 322 is disposed in valve 312, which is connected to vial 236 via conduit, such as tubing, 346. Then the 3-way valve 312 is switched to close nitrogen source 302 and open nitrogen source 304. A valve, for example a 2-way valve, 316 is then opened and the pressure of nitrogen source 304 is adjusted to a desired value with the aid of pressure gauge 314.

Figure 6:
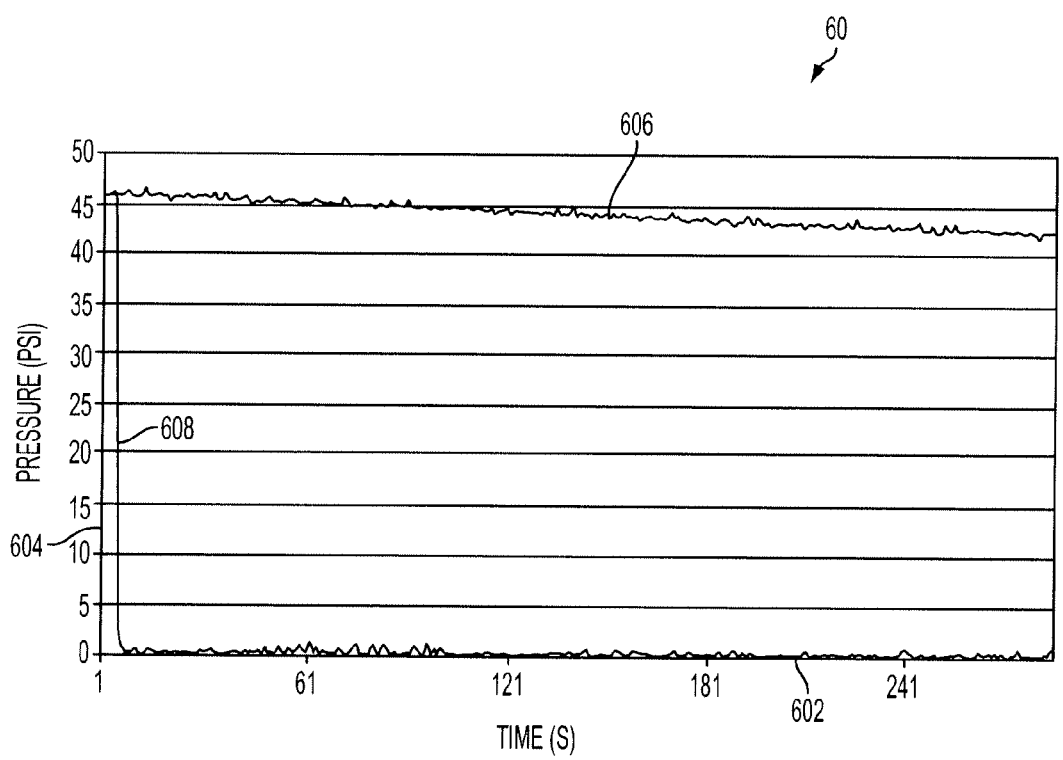
FIG. 6 shows membrane integrity test results in accordance with an embodiment of the present invention.

The 2-way valve 316 is then closed. The filter 318 is now in a closed, pressurized environment. If the filter membrane maintains its integrity, the pressure should be fairly constant, or drop slowly with time. For example the pressure for acceptable membrane integrity is typically greater than or equal to 50 psig. Otherwise a quick drop in pressure is observed. Results of the membrane integrity test are shown in FIG. 6.

Figure 4:
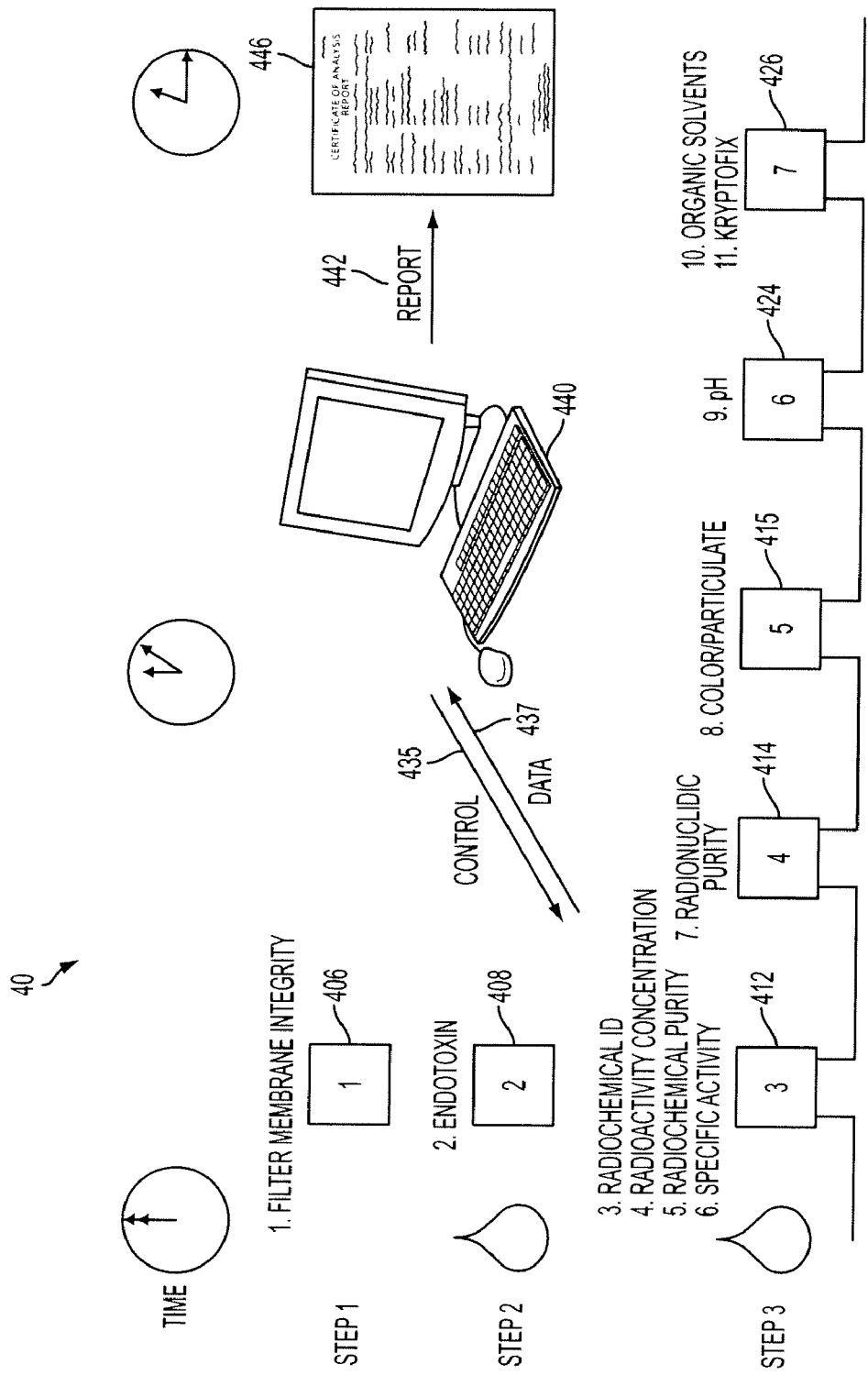
FIG. 4 shows a schematic for an automated radiochemical QC system.

FIG. 4 shows a schematic 40 of an automated radiochemical QC system. The modules shown in schematic 40 are used to complete a QC process in approximately 15 minutes thereby providing a PET tracer a Certificate of Analysis with 11 parameters. These 11 parameters are obtained through: 1.) pressure drop measurement; 2.) Endosafe-PTS measurement; 3.) HPLC analysis; 4.) decay measurement; 5.) color/particle measurement; 6.) pH measurement; and 7.) GC analysis. A computer, or processing terminal, controls the parallel QC processes and acquires data from all measurement stages, modules. As shown in FIG. 4, control commands are provided from computer 440 via communication medium 435 to each module, and data is provided from the testing modules to computer 440 via data communication medium 437. A report is generated at report, or certificate of analysis is provided by module 446, based on data received from computer 440 via communication path 442.

Specifically, module 406 shows that a filter membrane integrity test is performed. Module 408 shows that an endotoxin test is performed. Module 412 shows that a radiochemical identification test, radioactivity concentration test, radiochemical purity test and specific activity test are performed. Module 414 shows that a radionuclidic purity test is performed. Module 415 shows that color/particulate/clarity test is performed. Module 424 shows that a pH test is performed. Module 426 shows that an organic solvents test and Kryptofix test is performed.

FIG. 5 shows a schematic 50 including GC unit, HPLC unit, radioactivity detection unit for determining radionuclidic purity, color and appearance (clarity) unit and pH unit. FIG. 5 shows in-line HPLC related analyses for radiochemical identity; radiochemical purity; and specific activity test. The syringe 501 delivers sample solution to fill the GC injection valve 503, the HPLC injection valve 502 and the downstream detection/measurement units. Since the quantity of the sample is typically between approximately one nanoliter and approximately one microliter, the loading of the sample to HPLC and GC may be considered microfluidic. Furthermore, while the sample in the valve 502 and 503 is used for high performance liquid chromatography (HPLC) and GC related analysis, the sample in a section of the downstream tubing 508 underneath the radiation detection module 505 is used to record the decay of the radioactivity over a period of time. The decay recording is followed by an exponential curve fitting.

The GC unit includes a GC injection valve 503 that receives sample from syringe 501. The GC unit is used to determine organic solvent content and Kryptofix content analysis. Two additional parallel analyses, GC analysis for residual solvent volume and bacterial endotoxins concentration analysis, can be included to complete the QC system described herein. Instruments for both of these analyses are commercially available. While GC is capable of analyzing the content of organic impurities in a few minutes, the endosafe-pts from Charles River is a point-of-use test system providing quantitative endotoxin results in about 15 minutes. The sample sizes are from a few micro-liters for GC analysis and two 25 micro-liters for endotoxin test. A robotic system can be used for loading the sample into these testing modules. Both of these systems are integrated into the Auto QC instrument, thus avoiding the need for the user to perform manual injections, which are statistically the largest source of error during QC.

As an alternative to the GC-based test, the sample fills the Kryptofix test unit and mixes with iodine loaded by a syringe (not shown). The Kryptofix reacts with iodine, generating a colored substance which can be easily detected with a light source and a photo-detector. A T-shape micro-channel structure (shown in FIG. 10 herein) is designed to make sure a thorough mixing and quick detection of Kryptofix.

Figure 10:
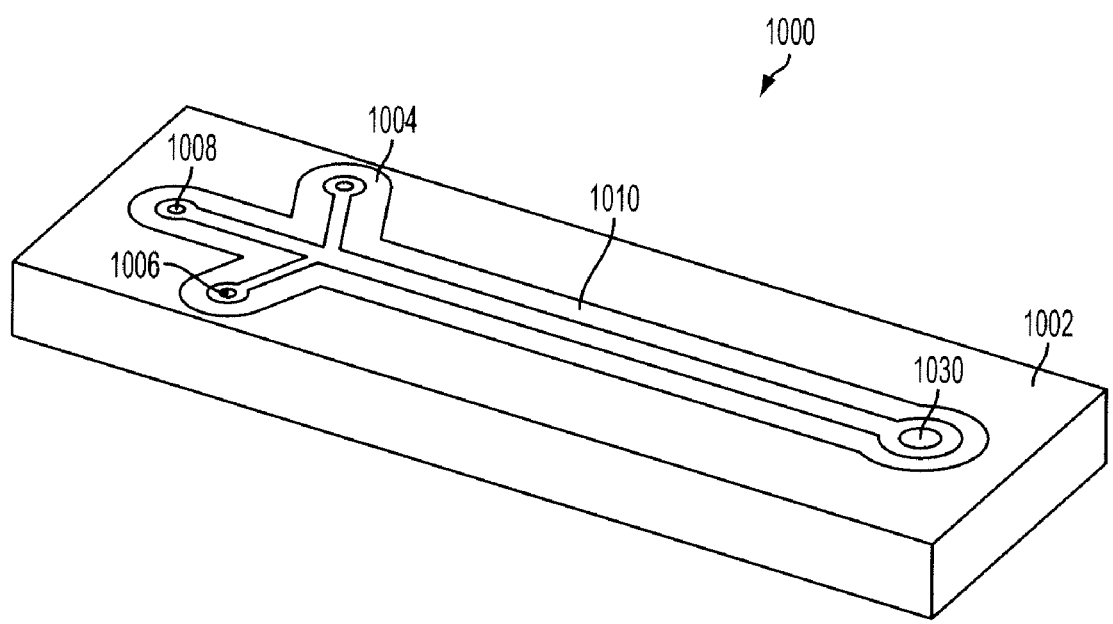
FIG. 10 shows a microfluidic structure used to characterize Kryptofix content in a sample in accordance with an embodiment of the present invention.

Alternatively, microfluidics can be used for Kryptofix test, which is based on mixing of laminar flow of three streams of fluid inside a small scale channel (1 mm wide, 100 µm deep) created on a 7.5 cm by 2.5 cm cast acrylic base (FIG. 10). A silicone adhesive is attached to the top surface of the base creating the end wall for the channel system. Two side ports are used for loading standard and sample solution while the middle port is used for iodine solution. As the solutions flow downstream the channel, diffusion, mixing and reaction progress. The developed color can be used to quantify the concentration of Kryptofix in sample as compared with that in standard.

The GC injection valve 503 then allows the sample to enter the HPLC unit via conduit, or tubing 511.

The HPLC unit is an analytical instrument which typically consists of a high pressure liquid pump (not shown), a loop valve 502 (shown in the inject position), loop 560, a column (not shown), and suitable detection units, to perform radiochemical identification test, radioactivity concentration test, radiochemical purity test and specific activity test. The HPLC unit has the resolving power to separate a mixture into individual components, making the subsequent analysis possible.

Each HPLC separation generates two traces in the chromatogram, a UV absorbance trace and a radioactivity trace. The retention time for the desired compound is defined as radiochemical identity. The radioactivity of the desired PET tracer from a fixed volume is called radioactivity concentration. On the radioactivity trace, the ratio of peak area of the desired compound to the total peak area of all compounds is defined as radiochemical purity. For desired compound, such as PET tracer, the peak area in the radioactivity trace over that in the UV trace translates into specific activity.

The radioactivity detection unit 505 is used for determining radionuclidic purity of the sample. The radioactivity signal from module 505 is used to determine radionuclidic purity of the sample. The sample reaches radioactivity detection module 505 via conduit 508. The half life, $T_{1/2}$ from the exponential equation of the fitted curve is an indication of the radionuclidic content and purity.

Embodiments of the present invention allow both the specific activity measurement (concentrated) and the radiochemical purity (dilute) to be performed with a single injection of a sample (see, for example, a representative schematic 1200 on FIG. 12). This is achieved by changing the sensitivity of the HPLC radiation detector based on the signal measured by the in-line radiation detector.

Color and appearance unit 580 analyzes the sample for particle (appearance) and color content. The color test typically uses a visible light source (not shown) and a spectrometer, for example a CCD spectrometer (not shown), both equipped with fiber optics. A colored test solution in the flow cell absorbs light at certain wavelength. The absorbance spectrum can be used to characterize the color of the sample. The CCD spectrometer is used to measure the appearance. Details of the color test are provided with respect to FIG. 13.

The color and appearance (clarity) tests may, alternatively, be microfluidic since they may occur in a capillary channel.

The pH unit 570 is typically a pH cell with a micro pH electrode, which is capable of micro-liter pH test. A valve, such as a 6 position, 7-port distribution valve (not shown) may be used to select solutions, including three standard pH solutions, for example, pH 4.01, pH 7.01 and pH 10.01, and an electrode storage solution. The three pH standards are used to routinely calibrate the pH electrode of the pH unit 570 while the storage solution is introduced into the pH unit 570 in case the pH electrode is not in use.

Waste location 552 is also shown. The sample is deposited in waste location 552 following the test procedure. Based on the results of the test of the sample, the remainder of the sample will either pass or fail the requirements for use.

Figure 7:
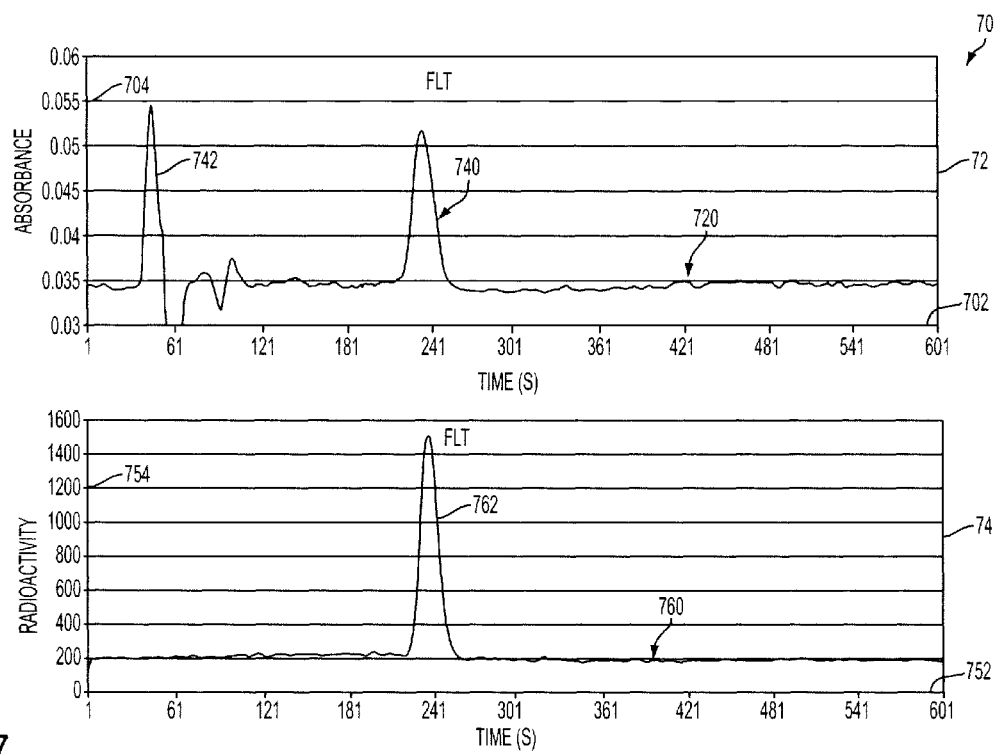
FIG. 7 shows UV absorbance and radioactivity chromagrams generated through HPLC separation an detection of [$^{18}$F] FLT in accordance with an embodiment of the present invention.

A sample chromatogram showing UV absorbance and radioactivity is exemplified on FIG. 7 herein.

An alternative option for the GC unit described above, involves a miniGC or a microGC which is chip based and contains an automated loading mechanism, eliminating the need for an injection syringe. The miniGC or micoGC are instruments that are miniaturized and specialized to perform a specified function. The devices are used separate and detect organic impurities.

Once the analysis of a sample has been performed, the results of all tests are analyzed automatically within the preset limits and the dose is qualified as passing or failing in each of the tests and overall. This information can be transferred to the user remotely (the user does not even need to be in the lab) and allow them to release the dose for human use.

For example, a technician can run the instrument and the report can be submitted to a pharmacist remotely. This way one pharmacist can validate/release doses in several locations involving minimal staff.

Finally when the full QC run has been completed, the system performs a self-cleaning and calibration cycle automatically, after which it is ready for the next run.

FIG. 6 shows membrane integrity test results 60 in accordance with an embodiment of the present invention. As shown in FIG. 6, time in units of seconds is shown on the X-axis 602 and pressure in units of psi are shown on the Y-axis 604. Line 606 shows a relatively slow pressure drop over time while line 608 shows a much faster relative pressure drop. When a filter membrane keeps its integrity, the pressure will drop according to line 606 rather than 608, which is a relatively precipitous drop in pressure. This is particularly evident within the initial 10 seconds.

FIG. 7 shows UV absorbance and radioactivity chromatograms 70 generated through HPLC separation and detection of [$^{18}$F] FLT in accordance with an embodiment of the present invention. As shown in FIG. 7, UV absorbance chromatogram 72 shows time in seconds on the X-axis 702 and absorbance coefficient is shown on the Y-axis 704. Line 720 shows the plot of UV absorbance. A first peak 742 is shown followed by peak 740 indicating the presence of FLT compound with a retention time of about 240 seconds.

Radioactivity chromatogram 74 shows time in seconds on the X-axis 752 and radioactivity range from 0 to 1600 is shown on the Y-axis 754. Line 760 shows a plot of the radioactivity. Peak 762 with radioactivity reading of approximately 1500 corresponds to FLT compound.

Figure 8:
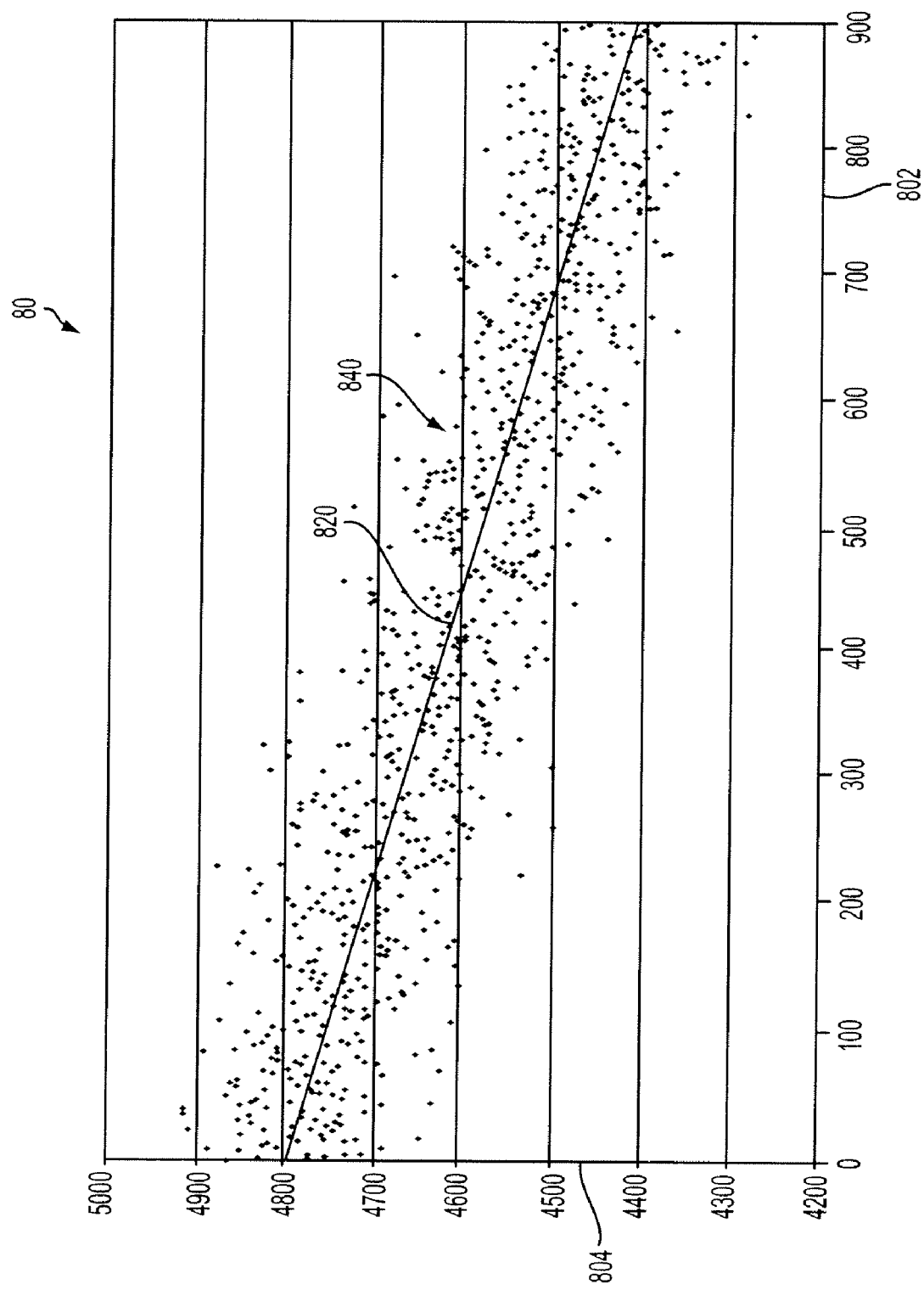
FIG. 8 shows radionuclidic test results based of decay measurement of [$^{18}$F] FLT in accordance with an embodiment of the present invention.

FIG. 8 shows radionuclidic test results 80 based of decay measurement of [$^{18}$F] FLT in accordance with an embodiment of the present invention. Time in seconds is shown on the X-axis 802 and radioactivity is shown on the Y-axis 804. Line 820 shows an exponential fit of decay of $^{18}$F FLT to the measured signal, represented by dots 840.

Figure 9:
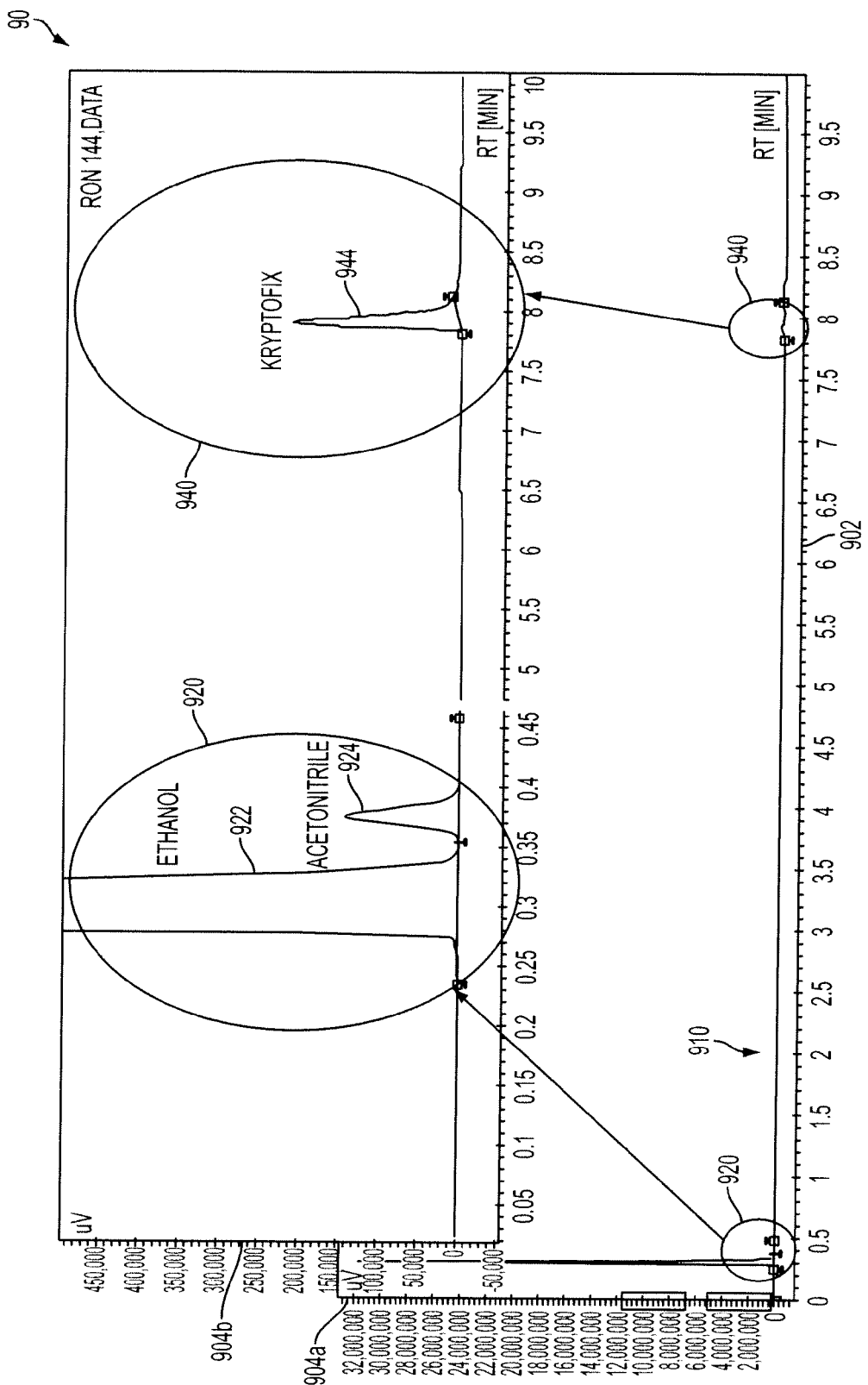
FIG. 9 shows ethanol, acetonitrile and Kryptofix test results in accordance with an embodiment of the present invention.

FIG. 9 shows ethanol, acetonitrile and Kryptofix GC test results 90 in accordance with an embodiment of the present invention. Time in seconds is shown on the X-axis 902 and ionization signal in μV is shown on the Y-axis 904. (Y-axis 904 includes 904(*a*) and 904(*b*), in which 904(*b*) is an expanded portion of 904(*a*).) Chromatogram 910 includes expanded portions 920 and 940. Expanded portion 920 includes peaks for ethanol 922 and acetonitrile 924. Expanded portion 940 shows the peak for Kryptofix 944. The Kryptofix test described herein is an automated test that incorporates two steps, previously performed separately, into a single GC operation. This is shown in FIG. 9 where both organic solvents (ethanol and acetonitrile) and Kryptofix are measured in a single GC operation.

FIG. 10 shows a microfluidic structure 1000 used to characterize Kryptofix content in a sample in accordance with an embodiment of the present invention. The structure 1000 includes substrate portion 1002 that includes three inlets 1004, 1006 and 1008 and a common waste outlet 1030. The middle inlet 1008 supplies iodine solution while the side inlets 1004, 1006 supply both sample solution and standard.

Channel 1010 provides a conduit or fluid path from inlets 1004, 1006 and 1008 to waste 1030. All devices are designed such that they can be operated either manually or automatically.

Figure 11:
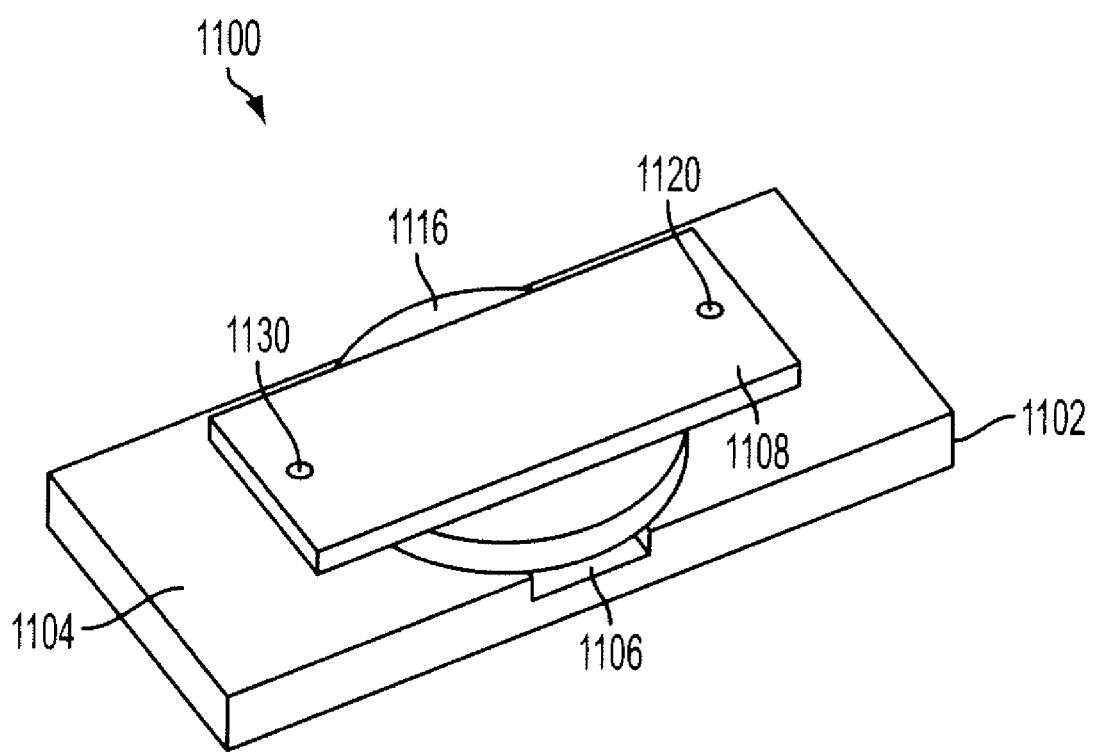
FIG. 11 illustrates a device to block venting holes of a filter in accordance with an embodiment of the present invention.

FIG. 11 illustrates a filter device 1100 where venting holes can be blocked in accordance with an embodiment of the present invention. The device 1100 includes a first rectangular plate 1102 and a second rectangular plate 1108. While the first plate 1102 and second plate 1108 are shown as rectangular in shape, any suitable shape may be used. The plate 1102 has an upper surface 1104 and a channel 1106. Plate 1108 is mounted on circular filter member 1116, and contains a membrane. Circular filter member 1116 is in proximity to surface 1104. Two holes, or vias, 1120 and 1130 are shown in plate 1108. These holes 1120, 1130 are used to tighten the two plates 1104 and 1108 together in order to seal the venting holes of the filter 1116.

FIG. 12 shows a schematic 1200 for test parameters according to an embodiment of the present invention. Syringe 1201 provides a single sample injection. The sample from syringe 1201 is provided to GC injection valve 1203, which can also receive Nitrogen. A compressed gas source 1209 is operatively coupled to the GC valve 1203. The sample from syringe 1201 fills the downstream modules, as shown herein. The sample also flows to HPLC injection valve 1202, via conduit 1211. HPLC injection valve 1202 may be in a loading mode or an injection mode. In a loading mode, the sample does not flow to loop 1260. In the injection mode, valve 1202 permits the sample to flow to loop 1260.

An HPLC pump 1240 is used to pump the sample through the HPLC column 1242. Loop 1260 and HPLC column 1242 are also shown. Conduit 1206, which is a flow channel, such as suitable tubing, provides sample to variable radiation sensitivity unit, or module 1212. The variable radiation sensitivity module 1212 includes a first radioactivity detection module 1204 and a second radioactivity detection module 1205. First radioactivity detection module 1204 receives a portion of the sample via conduit 1206 (which has come from HPLC column 1242. Second radioactivity detection module 1205 receives a portion of the sample via conduit 1208.

Based on the radioactivity signal from the second radioactivity detection module 1205, the length of tubing, or detection volume, underneath both radioactivity detection modules 1204, 1205 can be adjusted simultaneously with pneumatic actuators (not shown). This feature allows the radiation detectors (1204, 1205) to work in the linear detection range. This sensitivity adjustment only takes a few seconds, but it may save more than 10 minutes for an additional HPLC separation. (In manual QC, two HPLC injections may be required—concentrate sample for the specific activity and dilute sample for the radiochemical purity). As shown in FIG. 12, both of these analyses may be performed with a single sample injection from syringe 1201.

A sample portion from radioactivity detection module 1204 flows to UV detector 1228 for further testing and then to waste location 1250.

A sample portion from radioactivity detection module 1205 flows to an optical flow cell 1280 is used to test color and appearance. The color test uses a visible light source and a CCD spectrometer, both equipped with fiber optics. The color test is described in more detail above as well as with respect to FIG. 13.

The last portion of the sample fills a pH flow cell 1270, where a micro pH electrode is capable of micro-liter pH test. The pH test is described herein. (See FIG. 5.) The sample portion then flows to waste location 1252.

In another embodiment, the present invention provides a variable radiation sensitivity mechanism. In manual QC, two HPLC injections are usually required—a concentrated sample for the specific activity (or UV) and a dilute sample for the radiochemical purity. The embodiments of the current invention allow both of these analyses to be performed with a single sample injection. This can be accomplished by adjusting the radiation sensitivity, so the radiochemical analysis of a concentrated sample can be performed. Based on the radioactivity signal from the module 1212, the length of tubing, or detection volume, underneath both radioactivity detection modules (1204, 1205) can be adjusted simultaneously with pneumatic actuators (not shown). This feature allows the radiation detectors always work in the linear detection range. This sensitivity adjustment only takes a few seconds, but it may save more than 10 minutes for an additional HPLC separation.

Traditionally, GC is used for organic solvent analysis and iodine spot is used for Kryptofix test. The current invention combines the two in a single GC operation.

The GC sample can be injected either with a syringe, or a heated sample injection valve. The valve allows GC to be inline with the rest of test operation.

Figure 13:
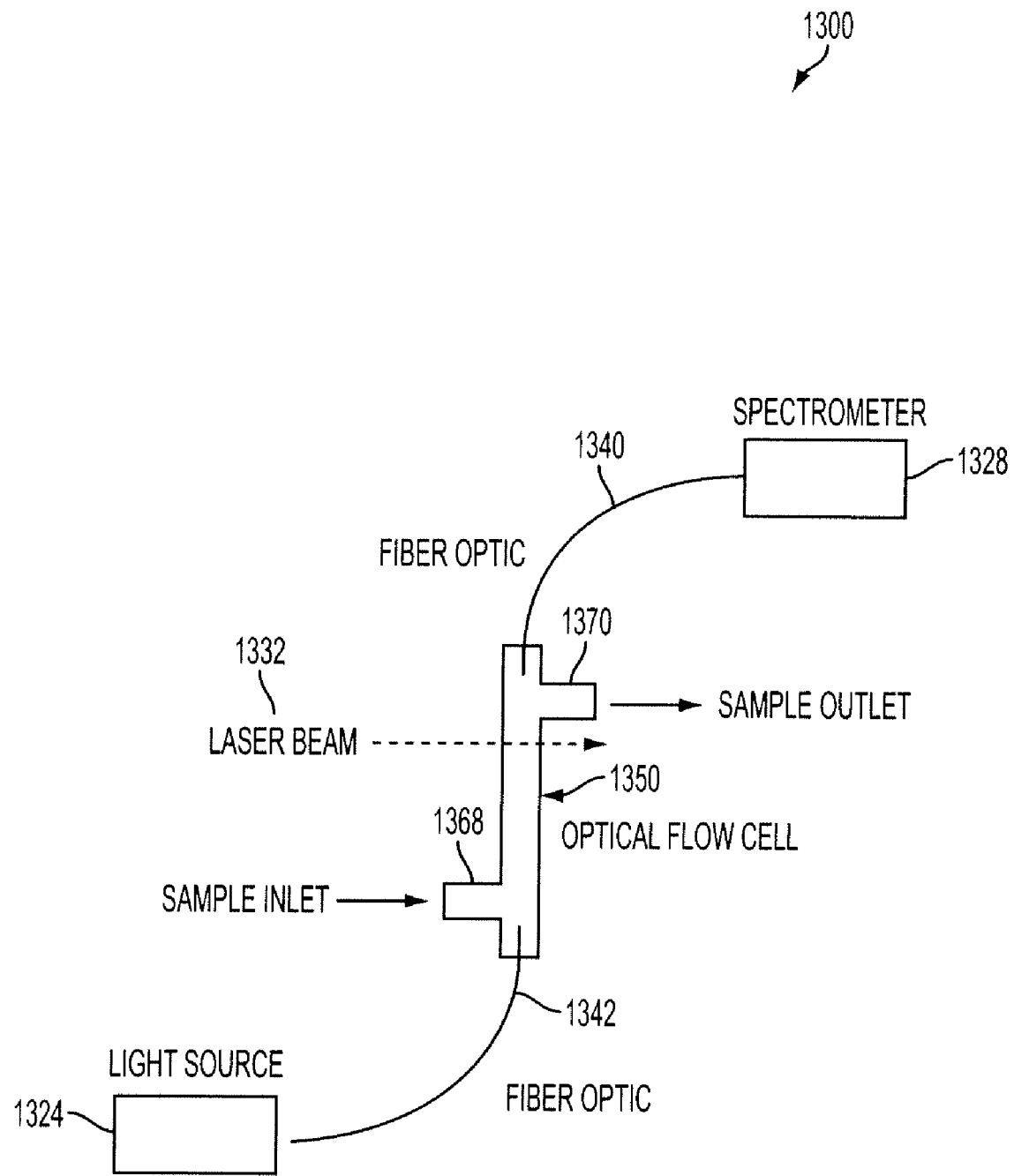
FIG. 13 shows a schematic for color and appearance test according to an embodiment of the present invention.

FIG. 13 shows a schematic 1300 for color and appearance test according to an embodiment of the present invention. A portion of the test sample is introduced to optical flow cell 1350 via sample inlet 1368. The color test uses a visible light source 1324 and a CCD spectrometer 1328, both equipped with fiber optics 1342 and 1340, respectively. A colored sample in the optical flow cell 1350 absorbs light at certain wavelength. The absorbance spectrum can be used to characterize the color of the sample. The CCD spectrometer 1328 may be used to measure the appearance. The light source for appearance is from a solid-state laser 1332, which is positioned substantially perpendicular to the detection fiber optic 1340. The degree of light scatter reflects the particulate content, or appearance, of the sample. Sample outlet 1370 provides an output for the test sample from optical flow cell 1350.

Figure 14:
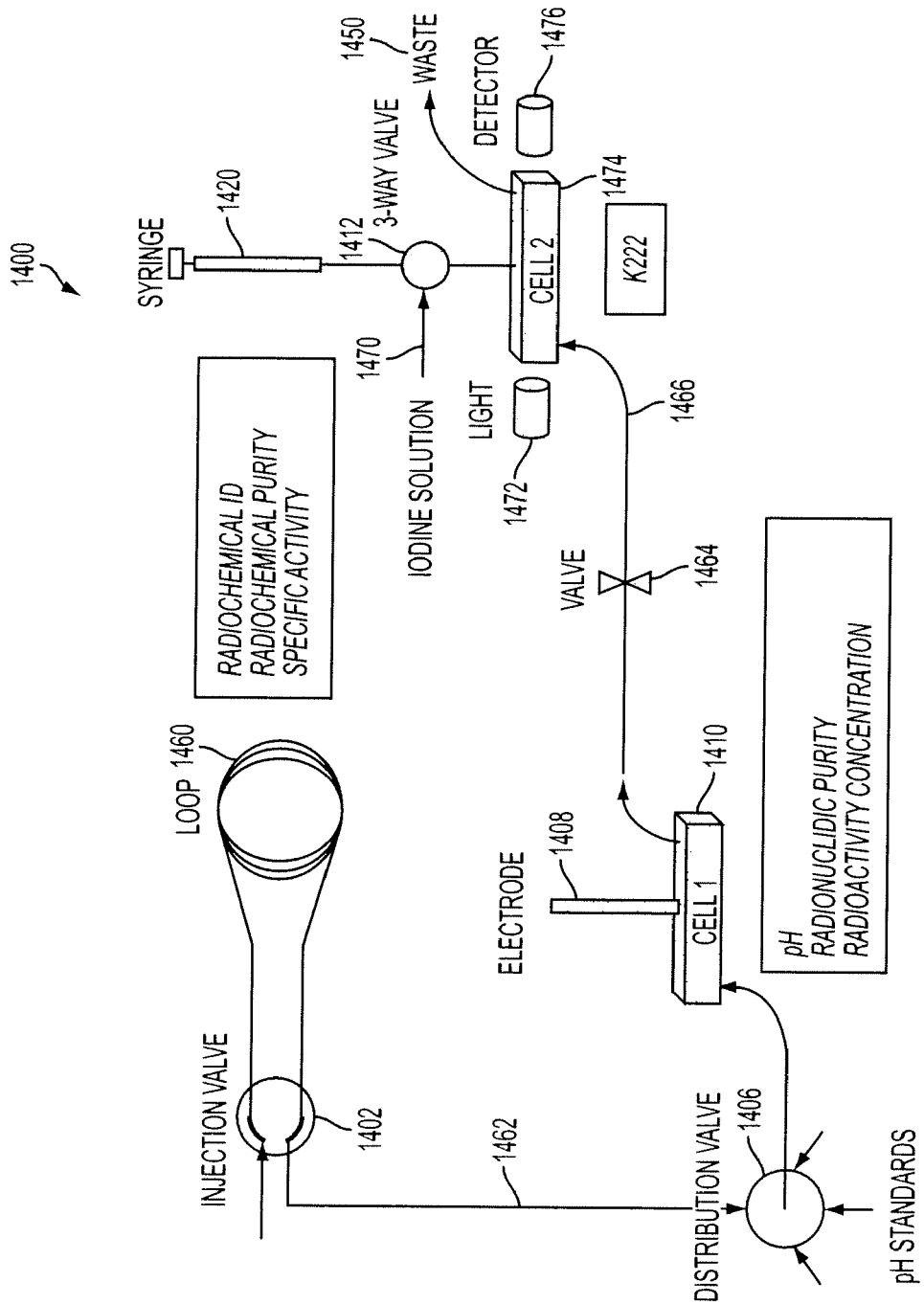
FIG. 14 shows an example of a QC system for a plurality of tests according to the present invention.

FIG. 14 shows a QC system 1400 for a plurality of tests according to the present invention. These tests include radiochemical identification, radiochemical purity, specific activity, pH, radionuclidic purity, radioactivity concentration, and K222.

System 1400 includes an injection valve 1402, used to inject sample from a single injection to loop 1460. In loop 1460, radiochemical identification, radiochemical purity and specific activity tests are performed.

The sample flows through conduit 1462 from loop 1460 to distribution valve 1406. A portion of sample is provided to a module 1410, having electrode 1408 for performing pH, radionuclidic purity and radioactivity concentration tests.

A portion of the sample flows through valve 1464 and tubing, or conduit, 1466 to K222 module 1474 for testing. The K222 module 1474 has an associated light source 1472 and detector 1476. Iodine is introduced via source 1470 to 3 way valve 1412. A portion of the sample may be drawn via syringe 1420. The portion may then flow to waste location 1450.

Figure 15:
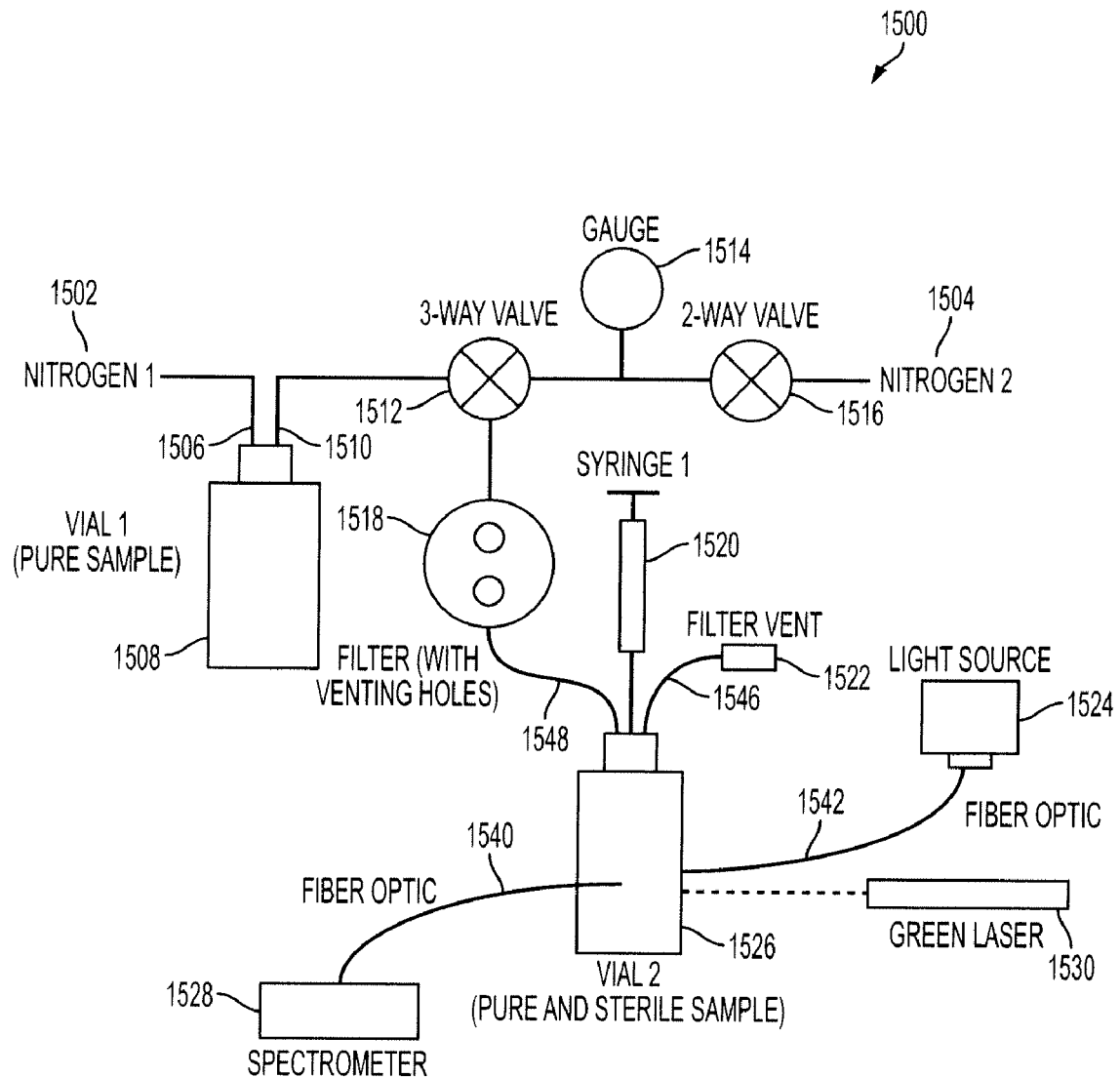
FIG. 15 shows a schematic for color and appearance test and a filter membrane integrity test.

FIG. 15 illustrates an example of a setup 1500 for performing a color and appearance test and a filter integrity test.

Typically, liquid pharmaceutical and biopharmaceutical products are sterilized by filtration. The sterilizing filtration process is designed to remove viable and non-viable particles from the liquid passing through the filter. The particles removed from the fluid either remain on the surface of the filter membrane or are trapped within the membrane matrix.

Integrity testing relies on the measurement of gas flow through wetted membranes. Diffusion of the test gas through the liquid filled pores in the membrane is a function of the diffusion constant and the solubility of the test gas in the liquid at the test temperature, the pressure differential of the test gas across the membrane, the thickness of the liquid layer, and the area and porosity of the membrane. Usually, after wetting the filter material, a gas pressure is applied to the inlet side and preferably the diffusive flow through the wetted filter material measured. The pressure is then measured in the outlet conduit as a function of time. It is then determined whether the pressure measured at a preselected time exceeds a reference pressure by a pre-determined amount. The filter is used to sterilize a sample, for example a PET tracer. This test is to make sure the filter membrane is still in good condition or maintains its integrity. Otherwise the PET tracer is questionable. While the test may damage the membrane, that is not critical or important at the test stage. The significance of the test is whether at a threshold pressure the filter is still acceptable or not.

It should be noted that the filter 318, features small venting holes. A filter device (shown in FIG. 11) is designed to block the venting holes at the time of the filter membrane integrity test. Otherwise, the venting holes remain open. Upon opening a valve, for example a 3-way valve, 1512 to nitrogen source 1502, the pressure from the nitrogen source 1502 pushes the purified sample solution out of the vial 1508 and fills the vial 1526 through the filter 1518, a process used to sterilize the tracer sample. An aliquot of the sample can be taken out from the vial 1526 for the following QC tests with the syringe 1520. The sterile sample vial may also be equipped with an additional filter vent 1522, which is connected to vial 1526 via conduit, such as tubing, 1546. Then the 3-way valve 1512 is switched to close nitrogen source 1502 and open nitrogen source 1504. A valve, for example a 2-way valve, 1516 is then opened and the pressure of nitrogen source 1504 is adjusted to a desired value with the aid of pressure gauge 1514.

The 2-way valve 1516 is then closed. The filter 1518 is now in a closed, pressurized environment. If the filter membrane maintains its integrity, the pressure should be fairly constant, or drop slowly with time. For example the pressure for acceptable membrane integrity is typically greater than or equal to 50 psig. Otherwise a quick drop in pressure is observed. Results of the membrane integrity test are shown in FIG. 6.

In addition to the membrane integrity test as described above, the sample in vial 1526 can be analyzed for particle (appearance) and color content. Color test uses a visible light source 1524 and a spectrometer 1528, shown as, for example a CCD spectrometer, both equipped with fiber optics, 1542 and 1540, respectively. A colored test solution in the flow cell absorbs light at certain wavelength. The absorbance spectrum can be used to characterize the color of the sample. The CCD spectrometer 1528 is used to measure the appearance.

The light source 1530 for appearance is from a solid-state laser, which is positioned perpendicular to the detection fiber optic. The degree of light scatter reflects the particulate content, or appearance, of the sample. The vial 1526 is of suitable optical quality, allowing optical absorbance and laser scatter to be adequately performed. In one embodiment, one fiber optic 1542 conducts the light from the light source 1524 to the vial 1526 and on an opposite side of the vial 1526 another fiber optic 1540 conducts the absorbed light to the spectrometer 1528. The degree of absorbance for a colored sample is wavelength dependent. In general, a colored sample absorbs light at one wavelength but not at the other.

The difference or the ratio in absorbance in the two wavelength regions determines the sample's color content. To determine the particle content, the light source 1524 can be blocked and the laser 1530 can be turned. The laser 1530 is located, for example approximately 90 degrees (perpendicular) to the fiber optic 1540 that is connected to the spectrometer 1528. The existence of particles scatters the laser light, which is detected with the spectrometer 1528. The intensity of the scattered light is related to the particle content, or appearance, of the sample.

Figure 16:
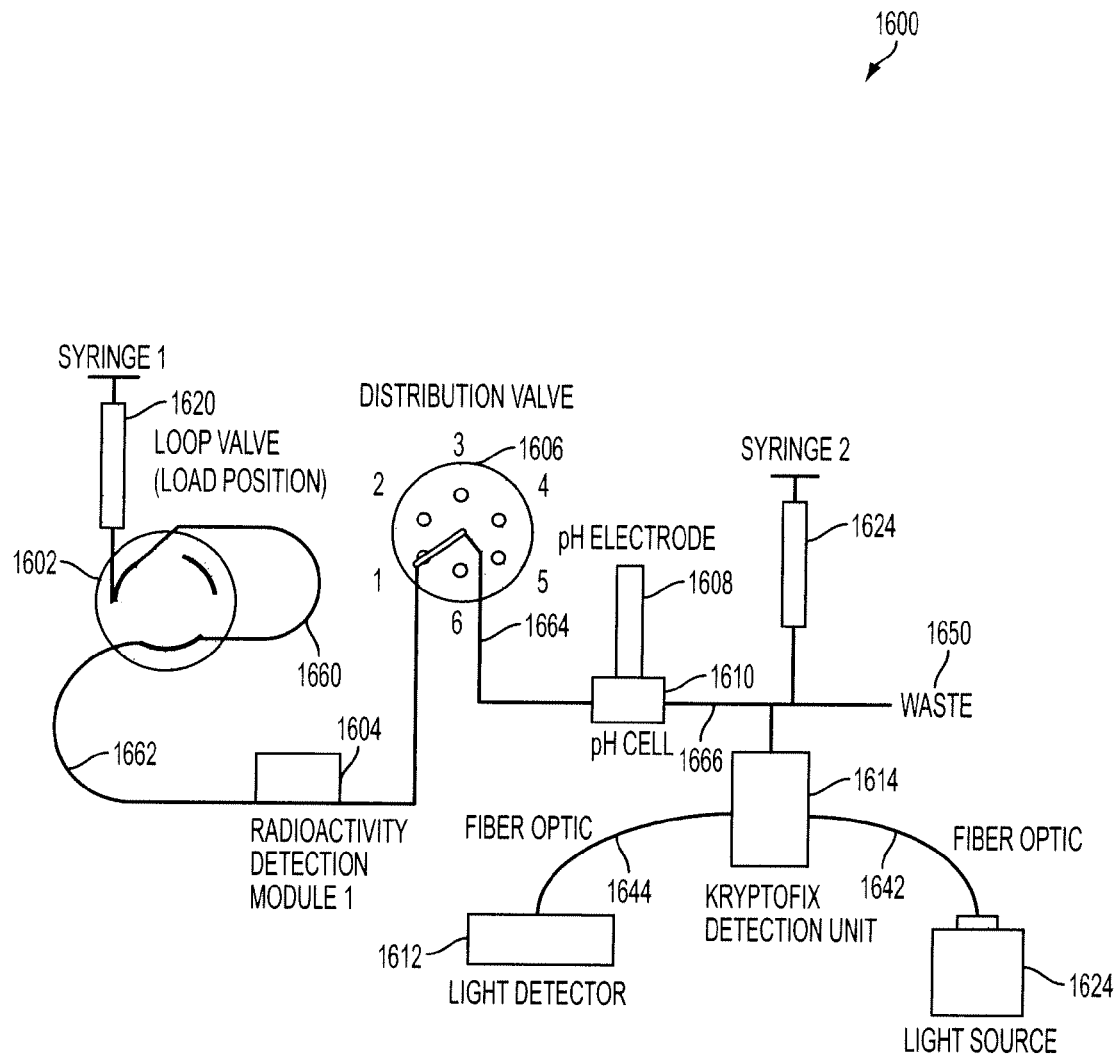
FIG. 16 shows a schematic for an automated radiochemical QC system radionuclidic purity test, radioactivity concentration test, pH test and Kryptofix test.

FIG. 16 shows a schematic 1600 for radionuclidic identity test, radioactivity concentration test, pH test and Kryptofix test. As shown in FIG. 16, syringe 1620 is used to deliver a sample for testing. A loop valve 1602 is operatively connected to syringe 1620 and sample loop 1660. As shown in FIG. 16, the loop valve 1602 is in a load position for loading the sample.

The syringe 1620 is used to deliver a few microliters of the sample solution to a GC for solvent analysis and for endotoxins test.

The syringe 1620 delivers sample solution to fill the sample loop 4160 and the downstream detection/measurement units. While the sample in the loop 1660 is used for high performance liquid chromatography (HPLC) related analysis, the sample in a section of the downstream tubing 1662 underneath the radiation detection module 1604 is used to record the decay of the radioactivity over a period of time. The decay recording is followed by an exponential curve fitting.

The half life, $T_{1/2}$, from the exponential equation of the fitted curve is an indication of the radionuclidic purity. The same module 1604 is used to determine the sample's radioactivity concentration, which is defined as the radioactivity per unit of solution volume. A distribution valve 1606 follows radioactivity detection module 1604.

Downstream from the distribution valve 1606, via tubing 1664, is a pH cell 1610 with a micro pH electrode 1608, which is capable of micro-liter pH test. The 6 position, 7-port distribution valve 1606 is used to select solutions, including three standard pH solutions, for example, pH 4.01, pH 7.01 and pH 10.01, and an electrode storage solution. The three pH standards are used to routinely calibrate the pH electrode 1608 while the storage solution is introduced into the pH cell 1610 in case the pH electrode 1608 is not in use.

The last portion of the sample fills the Kryptofix test unit 1614, and mixes with iodine loaded by the syringe 1624. The Kryptofix reacts with iodine, generating a colored substance which can be easily detected with a light source 1624 and a photo-detector 1612, both (1624, 1612) equipped with fiber optics 1642 and 1644, respectively. A T-shape micro-channel structure (shown in FIG. 10 herein) is designed to make sure a thorough mixing and quick detection of Kryptofix and iodine.

Figure 17:
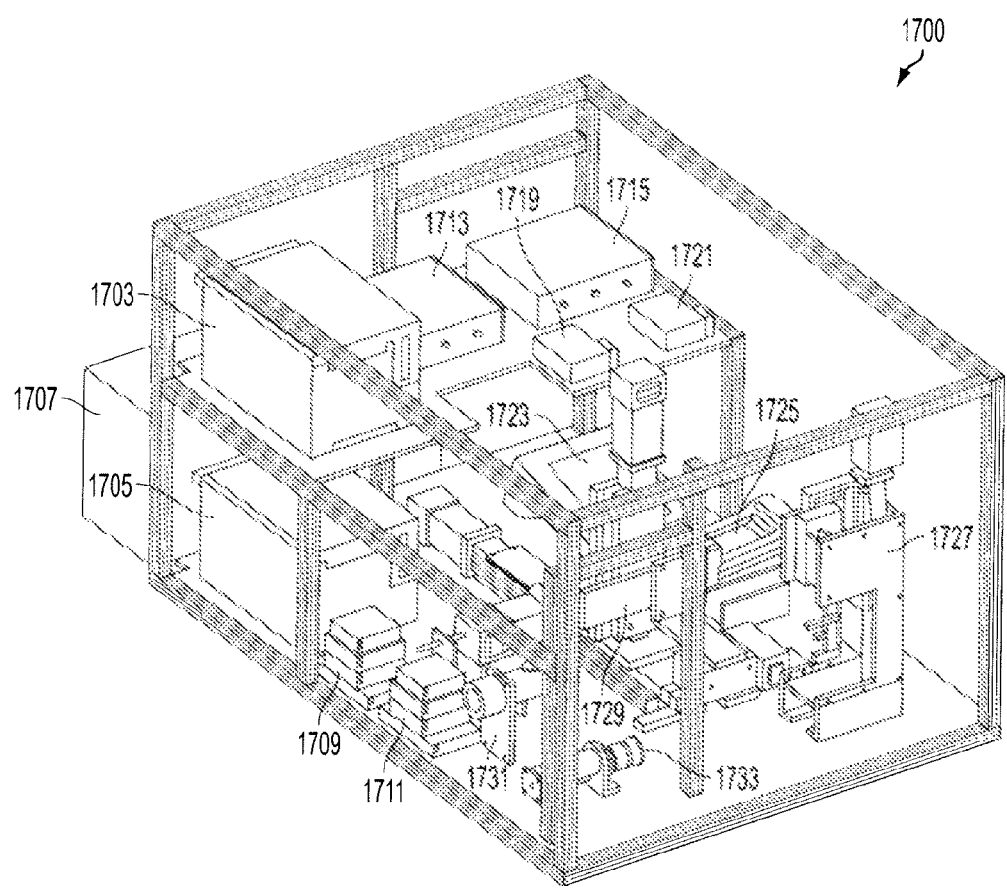
FIG. 17 shows a perspective view of an automated QC apparatus.

FIG. 17 shows a perspective view of an automated QC apparatus 1700. As shown in FIG. 17, apparatus 1700 includes a light source 1703 for the HPLC. A light source 1705 is used for testing color of the sample. HPLC pump 1707 and a radiation detectors 1709 and 1711 are shown. The radiation detector 1709 is used in conjunction with HPLC testing and radiation detector 1711 is used to detect radioactive decay of the sample. Radiation detector amplifiers 1713 and 1715 are also shown.

The apparatus 1700 also includes CCD light detectors 1719 and 1721 to detect light for testing as described herein. A pH testing module 1723 and endotoxin station 1725 are also shown.

Introduction station 1727 is used to introduce sample to apparatus 1700. The introduction station 1727 may be, for example an injection station so that sample may be injected using a syringe, alternatively the introduction station may be a fluid port that enables a sample from a vial or synthesis module to be provided to apparatus 1700. The apparatus may also include other fluid, electrical and/or mechanical ports to permit fluid, electrical and/or mechanical coupling of the apparatus 1700 to additional modules and/or devices. Thus, the apparatus 1700 may be operatively coupled to other modules to permit additional functions and testing.

A sample handling robot 1729 and rotary valves 1731 and 1733 are also shown.

The apparatus 1700 is, for example a self-contained portable unit and may be moved or transported. As stated above, the unit 1700 may have one or more communication ports, such as USB, or other connectors that permit the apparatus 1700 to be fluidically, mechanically and/or electronically connected to other modules, apparatus, or devices. For example the apparatus 1700 may be fluidically coupled to a synthesis module (not shown) used to originate a sample.

Alternatively, the apparatus may be coupled to a network to permit remote analysis of a sample and provide the test results to be transmitted to another location or destination. The apparatus 1700 may also receive samples from a vial, cartridge, tube or other suitable container, such as a transport vial, rather than a syringe. The vial, cartridge, tube or container may be radiation shielded to prevent exposure to radioactive material in the vial. This enables a technician, or operator, to transport or move or manipulate the sample, particularly between a synthesis module and the testing apparatus.

The embodiments illustrated herein are representative of in-line testing for all or any combination of the tests described.

After the above sample tests, the results are analyzed automatically to determine the dose quality—pass or fail based on pre-defined criteria. This information can be transferred to the user remotely (the user does not even need to be in the lab) and allow them to release the dose for human use.

| Item | Parameter | Range | Method |
| --- | --- | --- | --- |
| Sterility | Membrane filter integrity | $\geq 50$ psig | Pressure drop rate |
| Radiochemical identity | Retention time | Conforms or not | HPLC |
| Radiochemical purity | Area ratio - FLT and impurities | $\geq 95\%$ | HPLC |
| Specific activity | Area ratio - Counts/Abs. | $\geq 0.40$ Ci/mmol | HPLC |
| Organic solvents | (ethanol, acetonitrile) Volume % | 4.0-8.8%; $\leq 0.04\%$ | GC |
| Appearance | Color and clarity | Exceed threshold? | CCD/laser scattering |
| Radionuclidic purity | $T_{1/2}$ | 105-115 min | Decay monitoring |
| Radioactivity concentration | Counts/volume | 1-75 mCi/ml | Scintillation |
| pH | pH | 5.5-8.0 | Electrode |
| K222 | Concentration | $\leq 50$ μg/ml | Indicator reaction |
| Endotoxins | Concentration | $\leq 175$ EU/dose | Endosafe |

As an example, it has been demonstrated that an automated quality control run of a 18F-FLT radiotracer sample was complete in about 15 minutes. The issued report contained the following data:

| Test | Specification | Lot Results |
| --- | --- | --- |
| Appearance | Color and clarity: <10X standard deviation of reference | Color 2.43X standard deviation |
| Membrane filter Integrity test | 50 psi pressure drops to 0.5 its value in >3 minutes | 5.6 minutes |
| Radiochemical identity | Identity: HPLC retention time within +/−5% of standard | Conforms |
| Radiochemical Purity | $\geq 95\%$ | 100% |
| Specific Activity | $\geq 0.40$ Ci/μmol | 6.50 Ci/μmol |
| Radionuclidic Purity | $T_{1/2}$: 105-115 min | 109.9 min |
| Residual solvents | Ethanol: 4.0-8.8 weight % | 6.63% |
| | Acetonitrile: $\leq 0.04\%$ | 0% |
| Radioactivity Concentration | 1-75 mCi/mL at EOS | 28.4 mCi/mL |
| pH | 5.5-8.0 | 6.0 |
| K222 | $\leq 50$ μg/mL | 20 μg/mL |
| Endotoxins | $\leq 175$ EU/dose | 100 EU/dose |

In addition, the methods and devices in accordance with the various embodiments of the present invention may provide the following additional features and benefits:

These and other features of the apparatus allow the quality control of a large range of radiolabeled compounds using a microfluidic technology.

In an embodiment, a standard for appearance test, or clarity test is established as a function of particles per unit of volume, or an amount of particles per unit volume. While conventional testing for clarity was subjective, the present invention permits a standard threshold for a compound to be a certain amount of particles per unit volume. If the sample haws fewer particles per unit volume than the standard, the sample passes the clarity test. If the sample has more particles per unit volume than the standard, the sample fails the clarity test. The standard may be set by filtering a clear sample that will not exhibit any scattering. A minimum scattering may then be set for a compound.

In another embodiment, the measurement value of sterility as a function of membrane filter integrity, is a 50 psi drop too one-half its value in 5.6 minutes, which exceeds the 3 minute threshold.

In another embodiment, the measurement value of radiochemical purity, retention time is conforming, as seen by the result of 100 percent.

In another embodiment, the measurement value of radiochemical purity is no less than about 95%.

In another embodiment, the measurement value of specific activity, is no less than about 0.40 Ci/µmol.

In another embodiment, the measurement value of residual organic solvents concentration is no more than 0.04% v/v.

In another embodiment, the measurement value of color content and clarity or particle content is below the limit specified for each individual compound.

In another embodiment, the measurement value of radionuclidic purity for F-18, $T_{1/2}$, is about 105 to 115 min.

In another embodiment, the measurement value of radioactivity concentration is about 1 to about 75 mCi/mL.

In another embodiment, the measurement value of pH is in the range of about 5.5 to about 8.0.

In another embodiment, the measurement value of Kryptofix concentration does not exceed 50 µg/mL.

In another embodiment, the measurement value of endotoxins concentration does not exceed 175 EU/dose.

Generally, embodiments of the present invention are directed to methods and apparatus (system) for an automated quality control analysis of radiolabeled compounds, such as PET tracers, and to improve quality and efficiency of such operation.

In another embodiment, the invention provides a plurality of inline modules or testing devices configured to generate data about the analyzed substance. The inline structure of such system can be used to carry out a plurality of parallel tests on the same sample, which can be loaded into the sample line (tubing configured to deliver the same sample to various testing modules of the QC system at the same time). The sample line is being filled by a single sample injection.

In another embodiment, the present invention provides a GC test for both, residual volume of organic solvents and Kryptofix concentration. Traditionally, GC is used for organic solvent analysis and iodine spot is used for Kryptofix test. Current automated operation can encompass the two previously separate steps into a single GC operation.

It is an embodiment of the present invention that additional tests can be added as required by various compounds. Furthermore, not all tests are required for each compound. Indeed, not every compound will require each test described herein, yet may require other tests.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments.

The embodiments discussed herein were chosen and described in order to explain the principles and the nature of various embodiments and its practical application to enable one skilled in the art to utilize the present invention in various embodiments and with various modifications as are suited to the particular use contemplated. The features of the embodiments described herein may be combined in all possible combinations of methods, apparatus, modules, systems and computer program products.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for an integrated automated quality control analysis of a radioactive tracer compound comprising the following steps:
    utilizing a single sample injection, the single sample injection being a sample having a particular volume, for a plurality of inline quality control tests being conducted in a single pass;
    determining a sterility result via a filter membrane integrity test, the filter membrane integrity test being performed without use of the single sample injection and the sterility result being used to confirm filter membrane integrity;
    conducting a quantitative analysis of the single sample injection via the plurality of quality control tests;
    determining a measurement value of each of the plurality of quality control parameters;
    comparing each measurement value of the plurality of quality control parameters with a predetermined corresponding criterion value;
    determining a cumulative quality rating for the single sample injection based on the plurality of quality control tests and membrane integrity test;
    generating a quantitative report, that reflects a quantified result of the quality of the single sample injection against predetermined standards for the single sample injection, the report being based on the cumulative quality rating for the single sample injection; and
    releasing the quantitative report validating the single sample injection based on the quality rating,
    wherein the single sample injection is used for every control test required for the sample.

2. The method according to claim 1, wherein a plurality of quality control tests comprises determination of particle and color content.

3. The method according to claim 2, wherein a single optical cell is used for the determination of color.

4. The method according to claim 2, wherein a single optical cell is used for the determination of a color parameter and appearance parameter.

5. The method according to claim 1, wherein a plurality of quality control tests further comprises determination of radionuclidic purity.

6. The method according to claim 1, wherein a plurality of quality control tests further comprises determination of radioactive concentration.

7. The method according to claim 6, wherein the determination of radioactive concentration includes variable detection sensitivity.

8. The method according to claim 1, wherein a plurality of quality control tests further comprises determination of pH of the sample solution.

9. The method according to claim 1, wherein a plurality of quality control tests further comprises determination of Kryptofix concentration.

10. The method according to claim 9, wherein the determination of Kryptofix concentration includes a microfluidic test.

11. The method according to claim 1, wherein a plurality of quality control tests further comprises determination of radiochemical identity.

12. The method according to claim 1, wherein a plurality of quality control tests further comprises determination of radiochemical purity.

13. The method according to claim 1, wherein a plurality of quality control tests further comprises determination of specific activity of the sample.

14. The method according to claim 1, wherein a plurality of quality control tests further comprises determination of bacterial endotoxin concentration.

15. The method according to claim 1, wherein a plurality of quality control tests further comprises determination of residual solvent content.

16. The method according to claim 1, further comprising a GC test for determination of residual solvent content and Kryptofix.

17. The method according to claim 1, further comprising determining K222 concentration by GC.

18. The method according to claim 1, further comprising determining specific activity from a single HPLC injection.

19. The method according to claim 1, further comprising performing a microfluidic K222 test.

20. The method according to claim 1, wherein two or more tests are inline.

21. The method according to claim 1, wherein two or more tests performed in parallel.

22. The method according to claim 1, wherein the compound is a radiopharmaceutical.

23. The method according to claim 1, wherein the compound is a PET tracer.

24. An apparatus for automated quality control analysis of a radioactive tracer comprising the following elements:
an injection valve configured to deliver a single sample injection from a vial via a syringe in to a sample line;
at least one sample line containing the single sample injection for a plurality of quality control tests that are performed in a single pass, the tests including the following testing components;
a distribution valve for selecting solutions;
a filter membrane integrity test setup for performing an integrity test of the membrane;
an optical cell for performing color and/or appearance test connected to a light source and/or a laser and a spectrometer via fiber optics;
a HPLC column for determining specific activity from a single HPLC injection;
a UV cell connected to a UV light source and a UV detector via fiber optics;
a radioactivity detection module for determining purity of the sample;
a GC column, used for determining K222 concentration and solvent concentration from a single GC injection using the single sample injection;
a pH test cell for determining a pH of the sample solution,
one or more ports to operatively couple the elements to a computer system for quantitative processing of the experimental data and generation of a quantitative report that provides a quantitative result reflecting the quality of the single sample injection against predetermined standards.

25. The apparatus according to claim 24, wherein two or more elements are inline.

26. The apparatus according to claim 24, wherein two or more tests are run in parallel.

27. The apparatus according to claim 24, wherein two or more tests are run sequentially.

28. The apparatus of claim 24, capable of performing an automated self-cleaning and recalibration cycle.

29. The apparatus of claim 24 wherein the apparatus is portable.

30. The apparatus of claim 24 further comprising radiation shielding disposed proximal to one or more of the elements.

31. The apparatus of claim 24, wherein the computer system is located remotely from the apparatus.

32. A method for an integrated automated quality control analysis of a radioactive tracer compound comprising:
utilizing a single sample injection, the single sample injection being a sample having a particular volume, for a plurality of inline quality control tests being conducted in a single pass,
determining K222 concentration and solvent concentration from a single GC injection using the single sample injection;
conducting a quantitative analysis of the single sample injection via the plurality of quality control tests;
determining a measurement value of each of the plurality of quality control parameters;
comparing each measurement value of the plurality of quality control parameters with a predetermined corresponding criterion value;
determining a cumulative quality rating for the single sample injection based on the plurality of quality control tests;
generating a quantitative report, that reflects a quantified result of the quality of the single sample injection against predetermined standards for the single sample injection, the report being based the cumulative quality rating for the single sample injection; and
releasing the report validating the single sample injection based on the quality rating,
wherein the single sample injection is used for every control test required for the sample.

33. An apparatus for automated quality control analysis of a radioactive tracer comprising:
an injection valve configured to deliver a single sample injection from a vial via a syringe in to a sample line; and
at least one sample line containing the single sample injection for a plurality of quality control tests that are performed in a single pass, wherein the plurality of control tests quantitatively test multiple parameters to determine whether the single sample injection is acceptable based on predetermined criteria.

34. An apparatus for automated quality control analysis of a radioactive tracer comprising the following elements:
   an injection valve configured to deliver a single sample injection from a vial via a syringe in to a sample line;
   at least one sample line containing the single sample injection for a plurality of quality control tests that are performed in a single pass; and
   a filter membrane integrity test setup, wherein a measurement value for sterility based on the filter membrane integrity is determined after the single sample injection is delivered.

* * * * *